US010925469B2

(12) United States Patent
Kawano et al.

(10) Patent No.: US 10,925,469 B2
(45) Date of Patent: Feb. 23, 2021

(54) GUIDANCE APPARATUS AND CAPSULE MEDICAL APPARATUS GUIDANCE SYSTEM

(71) Applicant: OLYMPUS CORPORATION, Tokyo (JP)

(72) Inventors: Hironao Kawano, Machida (JP); Yuya Tanaka, Tokyo (JP)

(73) Assignee: OLYMPUS CORPORATION, Toyko (JP)

( * ) Notice: Subject to any disclaimer, the term of this patent is extended or adjusted under 35 U.S.C. 154(b) by 433 days.

(21) Appl. No.: 15/710,013

(22) Filed: Sep. 20, 2017

(65) Prior Publication Data

US 2018/0008131 A1    Jan. 11, 2018

Related U.S. Application Data

(63) Continuation of application No. PCT/JP2016/081757, filed on Oct. 26, 2016.

(30) Foreign Application Priority Data

Mar. 4, 2016   (JP) .............................. JP2016-042553

(51) Int. Cl.
   *A61B 1/00*   (2006.01)
   *A61B 34/00*  (2016.01)
   (Continued)

(52) U.S. Cl.
   CPC ...... *A61B 1/00158* (2013.01); *A61B 1/00016* (2013.01); *A61B 1/00045* (2013.01);
   (Continued)

(58) Field of Classification Search
   CPC ............ A61B 1/00002; A61B 1/00004; A61B 1/00147; A61B 1/00156; A61B 1/00158;
   (Continued)

(56) References Cited

U.S. PATENT DOCUMENTS 6,493,573 B1   12/2002   Martinelli et al.
7,580,739 B2   8/2009    Minai et al.
(Continued)

FOREIGN PATENT DOCUMENTS

JP   2002-556 A      1/2002
JP   2005-185499 A   7/2005
(Continued)

OTHER PUBLICATIONS

Decision To Grant A Patent dated May 9, 2017 received in 2017-513561.
(Continued)

*Primary Examiner* — Ryan N Henderson
(74) *Attorney, Agent, or Firm* — Scully, Scott, Murphy & Presser, P.C.

(57) ABSTRACT

A guidance apparatus includes: a magnetic field generator configured to generate a magnetic field that acts on a magnet; a magnetic field shielding material configured to shield the magnetic field generated by the magnetic field generator; an operation input device configured to receive an input of at least one of a target position and a target posture for guiding a position and a posture of a capsule medical apparatus; and a controller configured to control the magnetic field generator to generate a magnetic field that has been corrected to offset or reduce a deviation amount of the position or the posture of the capsule medical apparatus with respect to the target position or the target posture, caused by distortion, due to the magnetic field shielding material, of a magnetic field for guiding the capsule medical apparatus to at least one of the target position and the target posture.

17 Claims, 19 Drawing Sheets

(51) Int. Cl.
*A61B 1/04* (2006.01)
*A61B 5/06* (2006.01)

(52) U.S. Cl.
CPC .......... *A61B 1/00147* (2013.01); *A61B 1/041* (2013.01); *A61B 34/73* (2016.02); *A61B 5/062* (2013.01); *A61B 2034/731* (2016.02); *A61B 2034/733* (2016.02)

(58) Field of Classification Search
CPC ........... A61B 1/04; A61B 1/05; A61B 1/0615; A61B 1/273; A61B 1/2733; A61B 1/2736; A61B 1/31; A61B 1/041; A61B 5/062; A61B 5/073; A61B 34/73; A61B 2034/731; A61B 2034/733
See application file for complete search history.

(56) References Cited

U.S. PATENT DOCUMENTS

| | | |
|---|---|---|
| 7,783,441 B2 | 8/2010 | Nieminen et al. |
| 7,797,032 B2 | 9/2010 | Martinelli et al. |
| 8,290,572 B2 | 10/2012 | Martinelli et al. |
| 8,412,309 B2 | 4/2013 | Uchiyama et al. |
| 8,465,418 B2 | 6/2013 | Hasegawa et al. |
| 8,974,373 B2 | 3/2015 | Hasegawa et al. |
| 2008/0300458 A1 | 12/2008 | Kim et al. |
| 2011/0184690 A1* | 7/2011 | Iida ........................ A61B 1/041 702/150 |
| 2015/0065801 A1 | 3/2015 | Chiba et al. |

FOREIGN PATENT DOCUMENTS

| | | |
|---|---|---|
| JP | 2006-523473 A | 10/2006 |
| JP | 2007283001 A | 11/2007 |
| JP | 2008-503310 A | 2/2008 |
| JP | 2009-39356 A | 2/2009 |
| WO | 2004/091391 A1 | 10/2004 |
| WO | 2005/122866 A1 | 12/2005 |
| WO | 2013/168710 A1 | 11/2013 |

OTHER PUBLICATIONS

International Search Report dated Dec. 13, 2016 received in PCT/JP2016/081757.

* cited by examiner

FIG.14
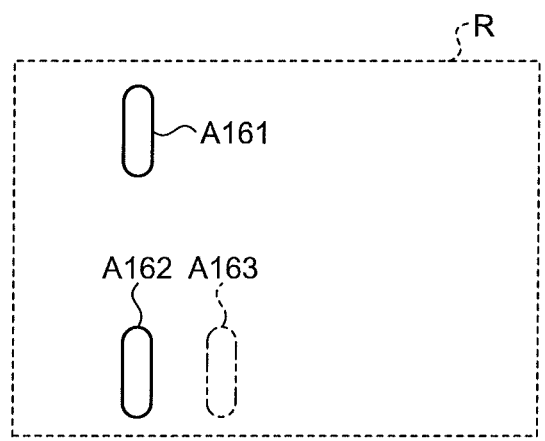
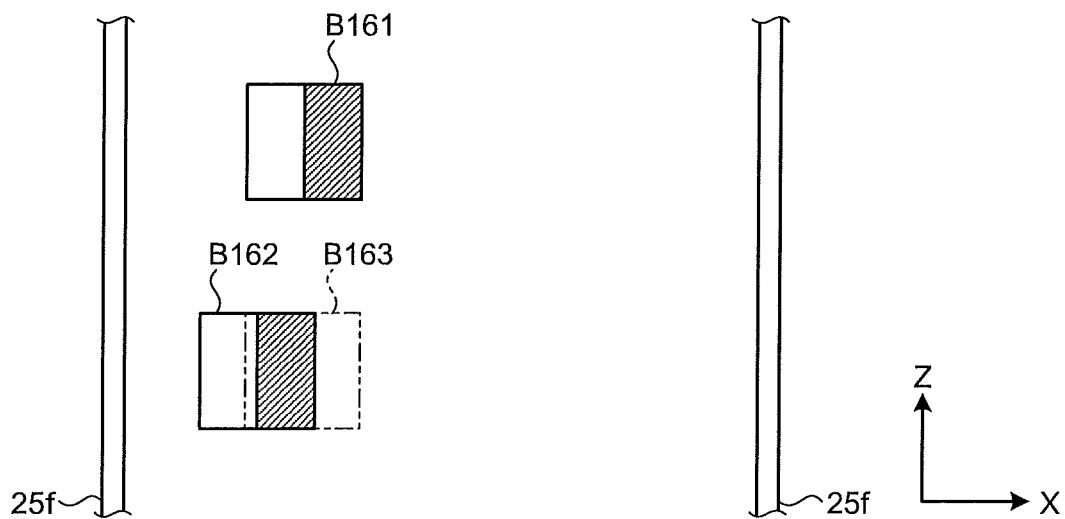

FIG.16
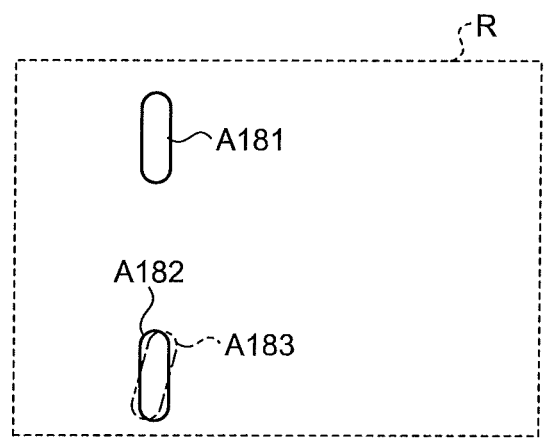
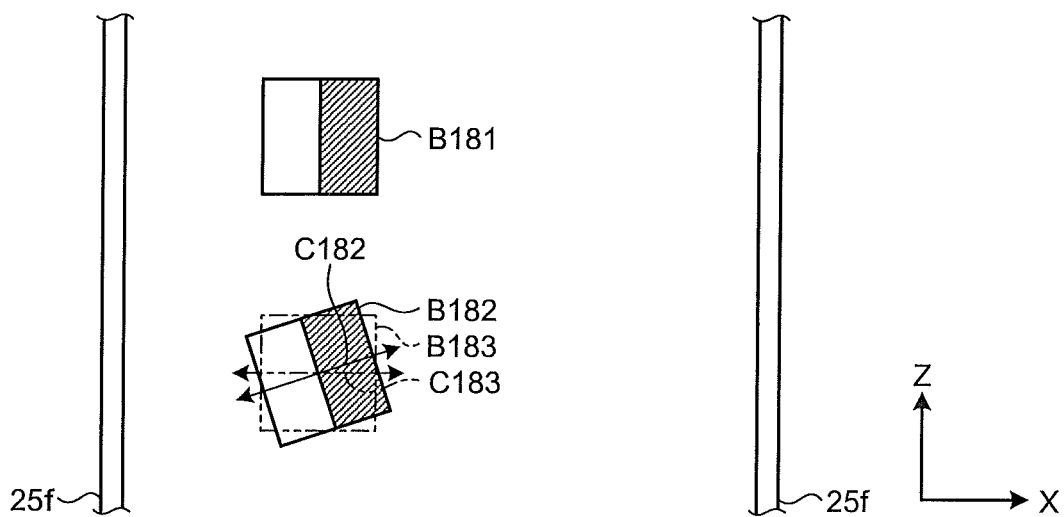

GUIDANCE APPARATUS AND CAPSULE MEDICAL APPARATUS GUIDANCE SYSTEM

CROSS-REFERENCE TO RELATED APPLICATION

This application is a continuation of PCT International Application No. PCT/JP2016/081757 filed on Oct. 26, 2016 which claims the benefit of priority from Japanese Patent Application No. 2016-042553 filed on Mar. 4, 2016, the entire contents of which are incorporated herein by reference.

BACKGROUND

1. Technical Field

The disclosure relates to a guidance apparatus and a capsule medical apparatus guidance system.

2. Related Art

Conventionally, a capsule medical apparatus that is introduced into a subject and obtains various types of information related to the subject, or that administers a drug, or the like, to the subject, has been developed. A known example of this is a capsule endoscope formed into a size that can be introduced into the gastrointestinal tract of the subject.

The capsule endoscope has an imaging function and a wireless communication function inside a capsule-shaped casing. The capsule endoscope is swallowed by the subject and thereafter captures images while moving inside the gastrointestinal tract by a peristaltic motion, or the like, and wirelessly transmits image data of the image of an internal portion of an organ of the subject (hereinafter, also referred to as an in-vivo image) in sequence. The wirelessly transmitted image data are received by a receiving device provided outside the subject, taken into an image display device such as a workstation, and undergo predetermined image processing. With this procedure, the in-vivo image of the subject can be displayed as a still image or a moving image on the screen of the image display device.

In recent years, a guidance system including a guidance apparatus for guiding a capsule endoscope introduced into a subject by a magnetic field has been proposed (refer to, for example, WO 2005/122866 A). Generally, such a guidance system includes a permanent magnet provided inside the capsule endoscope, while including a magnetic field generator such as an electromagnet or a permanent magnet provided in the guidance apparatus. Liquid such as water is introduced into the gastrointestinal tract such as the stomach of the subject and the capsule endoscope inside the subject is guided by a magnetic field generated by the magnetic field generator in a state where the capsule endoscope is drifting in the liquid. By providing the guidance system with a display unit for receiving the image data obtained by the capsule endoscope and displaying the in-vivo image, a user can operate to guide the capsule endoscope using an operation input device provided on the guidance apparatus with reference to the in-vivo image displayed on the display unit.

SUMMARY

In some embodiments, a guidance apparatus configured to guide a capsule medical apparatus that is introduced into a subject and that internally includes a magnet, by a magnetic field, is provided. The guidance apparatus includes: a magnetic field generator configured to generate a magnetic field that acts on the magnet for guiding the capsule medical apparatus; a magnetic field shielding material configured to shield the magnetic field generated by the magnetic field generator; an operation input device configured to receive an input of at least one of a target position and a target posture for guiding a position and a posture of the capsule medical apparatus; and a controller configured to control the magnetic field generator to generate a magnetic field that has been corrected to offset or reduce a deviation amount of the position or the posture of the capsule medical apparatus with respect to the target position or the target posture, caused by distortion, due to the magnetic field shielding material, of a magnetic field for guiding the capsule medical apparatus to at least one of the target position and the target posture.

In some embodiments, a capsule medical apparatus guidance system includes: the guidance apparatus; and a capsule medical apparatus including a magnet being internally arranged.

The above and other features, advantages and technical and industrial significance of this disclosure will be better understood by reading the following detailed description of presently preferred embodiments of the disclosure, when considered in connection with the accompanying drawings.

BRIEF DESCRIPTION OF THE DRAWINGS

FIG. 14 is a diagram for explaining a method for controlling an external permanent magnet of a guidance apparatus according to Example 6;

FIG. 16 is a diagram for explaining a method for controlling an external permanent magnet of a guidance apparatus according to Example 8;

DETAILED DESCRIPTION

Figure 1:
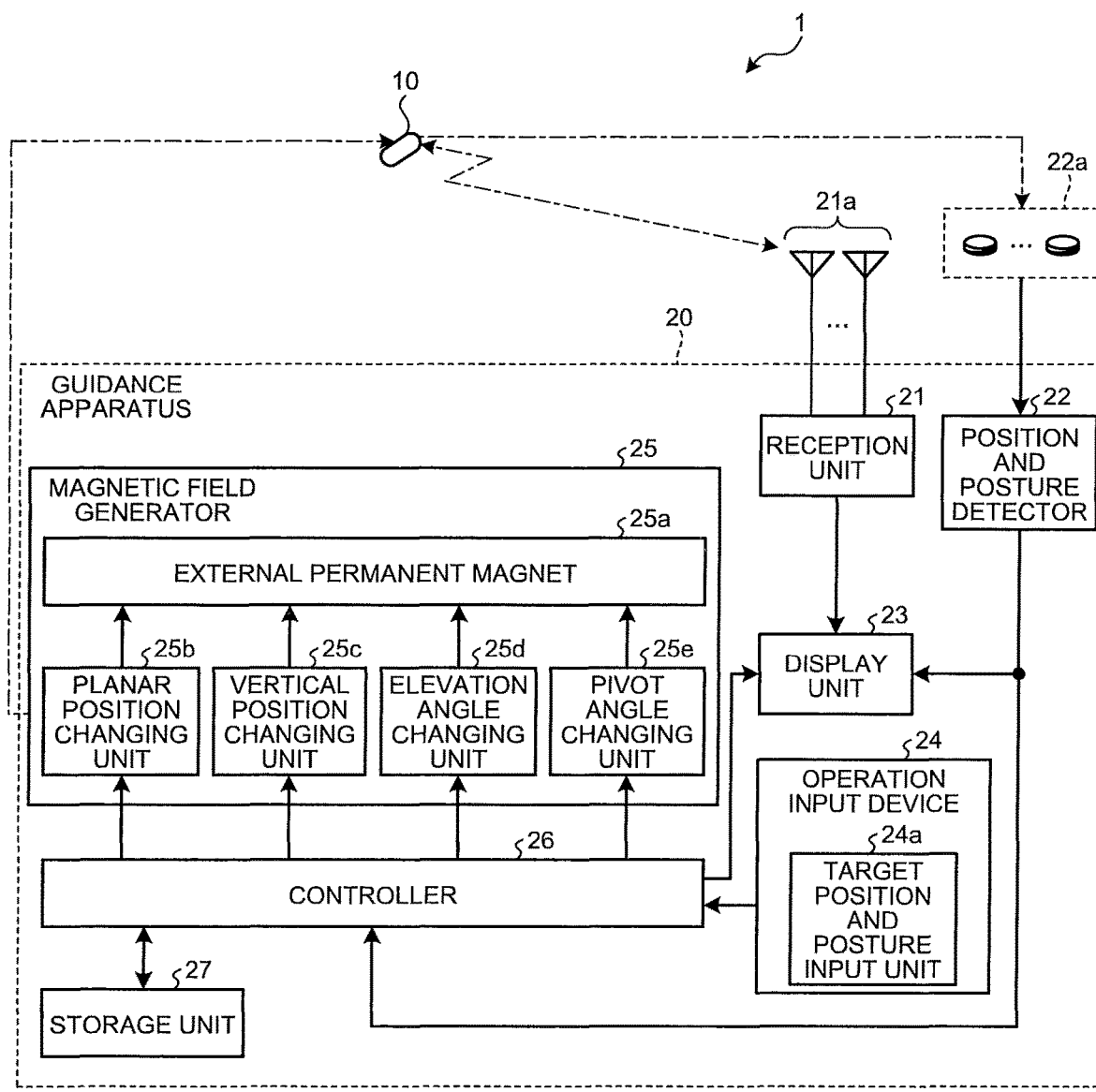
FIG. 1 is a diagram illustrating an exemplary configuration of a guidance apparatus and a capsule medical apparatus guidance system according to an embodiment of the disclosure.

Hereinafter, a guidance apparatus and a capsule medical apparatus guidance system according to an embodiment of the disclosure will be described with reference to the drawings. The following description will exemplify a capsule endoscope configured to be introduced into the subject orally and to capture an image of the inside of the gastrointestinal tract of the subject as one mode of a capsule medical apparatus as a guidance target by the capsule medical apparatus guidance system according to the present embodiment. The disclosure, however, is not limited to this embodiment. In other words, the disclosure is applicable to guidance for various capsule-shaped medical apparatuses such as a capsule endoscope that moves inside the lumen from the esophagus to the anus of the subject, a capsule medical apparatus that delivers a drug, or the like, to internal portions of the subject, and a capsule medical apparatus including a pH sensor for measuring pH within the subject.

Note that the drawings in the following description merely schematically illustrate the shapes, sizes, and positional relations to such degrees that the contents of the disclosure are understandable. Accordingly, the disclosure is not limited solely to the shapes, sizes, and positional relations exemplified in the individual drawings. In the drawings, same reference signs are attached to the same portions.

Embodiment

FIG. 1 is a diagram illustrating an exemplary configuration of a guidance apparatus and a capsule medical apparatus guidance system according to an embodiment of the disclosure. As illustrated in FIG. 1, a capsule medical apparatus guidance system 1 according to the present embodiment includes a capsule endoscope 10 and a guidance apparatus 20. The capsule endoscope 10 is a capsule medical apparatus to be introduced into a body cavity of a subject and internally includes a permanent magnet. The guidance apparatus 20 generates a magnetic field and guides the capsule endoscope 10 introduced into the subject.

The capsule endoscope 10 is introduced into the organs of the subject together with a predetermined liquid by oral ingestion, or the like, and thereafter, moves inside the gastrointestinal tract and is finally discharged to the outside of the subject. The capsule endoscope 10 drifts in the liquid introduced into the organs such as the stomach of the subject, sequentially captures an in-vivo image while being guided by the magnetic field, and sequentially and wirelessly transmits image data corresponding to the in-vivo image obtained by the imaging.

Figure 2:
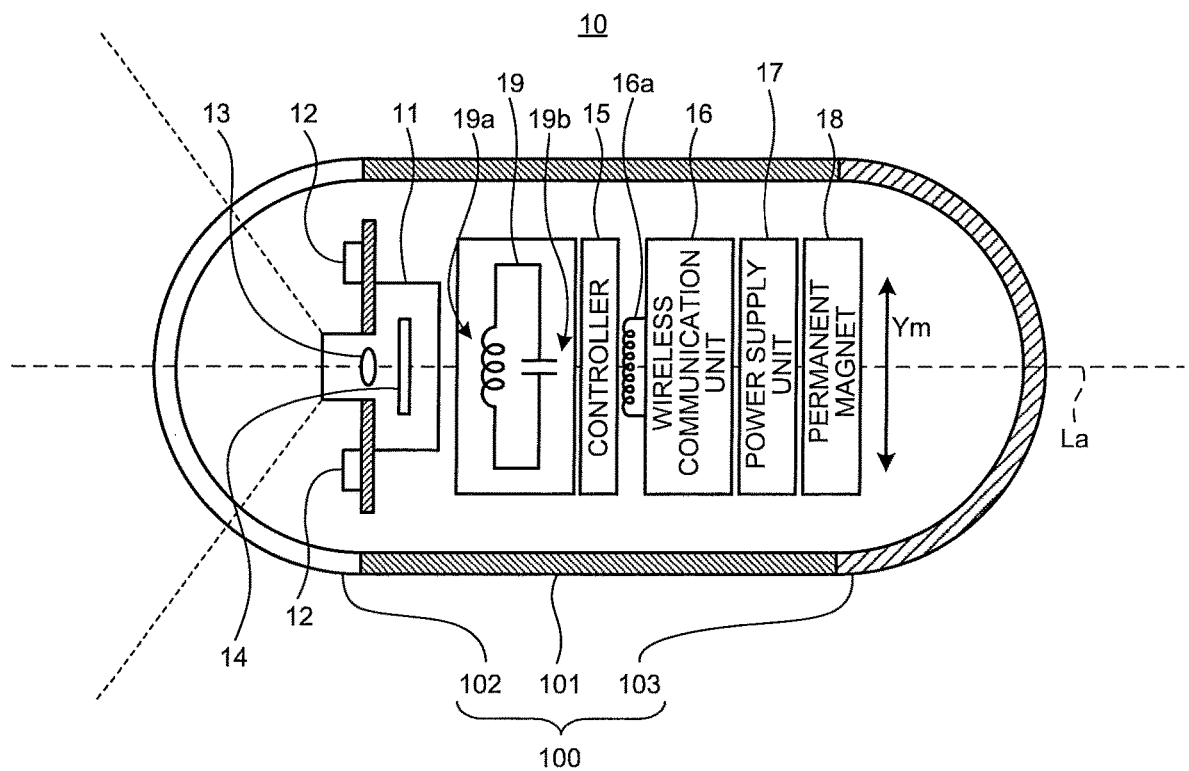
FIG. 2 is a schematic diagram illustrating an exemplary internal structure of a capsule endoscope illustrated in FIG. 1.

FIG. 2 is a schematic diagram illustrating an exemplary internal structure of the capsule endoscope illustrated in FIG. 1. As illustrated in FIG. 2, the capsule endoscope 10 includes a capsule-shaped casing 100, an imaging unit 11, a controller 15, a wireless communication unit 16, a power supply unit 17, a permanent magnet 18, and a position detection magnetic field generator 19. The capsule-shaped casing 100 is an outer casing formed to have a size to be easily introduced into an internal organ of a subject. The imaging unit 11 outputs an image signal of which the inside of the subject is captured. The controller 15 processes the image signal output by the imaging unit 11 and controls each of components of the capsule endoscope 10. The wireless communication unit 16 wirelessly transmits the image signal processed by the controller 15 to the outside of the capsule endoscope 10. The power supply unit 17 supplies electric power to each of the components of the capsule endoscope 10. The permanent magnet 18 enables guidance by the guidance apparatus 20. The position detection magnetic field generator 19 generates a position detection magnetic field, that is, a magnetic field used for detecting the position of the capsule endoscope 10.

The capsule-shaped casing 100 is an outer casing formed into a size that can be introduced into the internal organ of the subject, and includes a cylindrical casing 101 and dome-shaped casings 102 and 103. The capsule-shaped casing 100 is configured by block opening ends on both sides of the cylindrical casing 101 with the dome-shaped casings 102 and 103. The cylindrical casing 101 and the dome-shaped casing 103 is a casing substantially opaque for visible light. In contrast, the dome-shaped casing 102 is an optical member having a dome-like shape, transparent to the light having a predetermined wavelength band, such as visible light. As illustrated in FIG. 2, the capsule-shaped casing 100 encapsulates, using fluid-tight sealing, an imaging unit 11, a controller 15, a wireless communication unit 16, a power supply unit 17, a permanent magnet 18, and a position detection magnetic field generator 19.

The imaging unit 11 includes an illumination unit 12 such as an LED, an optical system 13 such as a condenser lens, and an imaging element 14, that is, a CMOS image sensor, a CCD, or the like. The illumination unit 12 projects illumination light such as white light toward an imaging field of the imaging element 14, thereby illuminating the subject within the imaging field through the dome-shaped casing 102. The optical system 13 collects reflected light from the imaging field onto an imaging surface of the imaging element 14 and forms an image. The imaging element 14 converts reflected light from the imaging field, received on the imaging surface, into an electrical signal, and outputs it as an image signal.

The controller 15 controls each of operation of the imaging unit 11 and the wireless communication unit 16, and controls input and output of signals between these components. Specifically, the controller 15 causes the imaging element 14 to image the subject in the imaging field illuminated by the illumination unit 12, and performs predetermined signal processing on the image signal output from the imaging element 14. Furthermore, the controller 15 causes the wireless communication unit 16 to wirelessly transmit in time sequence the image signal that has undergone signal processing.

The wireless communication unit 16 obtains the image signal of the in-vivo image output by the imaging unit 11 from the controller 15, and performs modulation processing, or the like, on the image signal and generates a radio signal. The wireless communication unit 16 includes an antenna 16a for transmitting a radio signal, and wirelessly transmits the generated radio signal via the antenna 16a.

The power supply unit 17 is a power storage unit such as a button cell battery and a capacitor, including a switching unit such as a magnetic switch and an optical switch. In a case where the power supply unit 17 includes a magnetic switch, the power supply unit 17 switches the on/off state of the power supply by a magnetic field applied from the outside. In the case of the on state, the power supply unit 17 appropriately supplies electric power of the power storage unit to each of the components of the capsule endoscope 10, that is, the imaging unit 11, the controller 15, and the wireless communication unit 16. Moreover, in the case of the off state, the power supply unit 17 stops power supply to each of the components of the capsule endoscope 10.

The permanent magnet 18 is provided to enable guidance of the capsule endoscope 10 by the magnetic field generated by a magnetic field generator 25 described below. The permanent magnet 18 is arranged such that the center of gravity of the capsule endoscope 10 and the geometrical center of the capsule-shaped casing 100 are different from each other. Moreover, the permanent magnet 18 is fixedly arranged in the capsule-shaped casing 100 such that a magnetic pole direction Ym is inclined with respect to a long axis La. That is, the magnetic pole direction of the permanent magnet 18 is different from the direction of a line connecting the center of gravity of the capsule endoscope 10 with the geometrical center of the capsule-shaped casing 100. In the present embodiment, the permanent magnet 18 is arranged such that the magnetic pole direction Ym is orthogonal to the long axis La. The permanent magnet 18 operates to follow the magnetic field applied from the outside, making it possible to achieve guidance of the capsule endoscope 10 by the magnetic field generator 25.

The position detection magnetic field generator 19 constitutes a portion of a resonant circuit and includes a marker coil 19a and a capacitor 19b. The marker coil 19a generates a magnetic field by the current flow. The capacitor 19b forms the resonant circuit together with the marker coil 19a. The position detection magnetic field generator 19 receives power supplied from the power supply unit 17 and generates a position detection magnetic field having a predetermined frequency.

Referring again to FIG. 1, the guidance apparatus 20 includes a reception unit 21, a position and posture detector 22, a display unit 23, an operation input device 24, a magnetic field generator 25, a controller 26, and a storage unit 27. The reception unit 21 performs wireless communication with the capsule endoscope 10 and receives a radio signal including an image signal transmitted from the capsule endoscope 10. The position and posture detector 22 detects the position and posture of the capsule endoscope 10 in the subject on the basis of the position detection magnetic field generated by the position detection magnetic field generator 19 of the capsule endoscope 10. The display unit 23 obtains an image signal from the radio signal received by the reception unit 21 and performs predetermined signal processing on the image signal and displays an in-vivo image, and displays information indicating the position and the posture of the capsule endoscope 10 in the subject. The operation input device 24 receives an input of information for instructing various types of operation in the capsule medical apparatus guidance system 1, or the like. The magnetic field generator 25 generates a magnetic field for guiding the capsule endoscope 10. The controller 26 controls these components. The storage unit 27 stores image data of the in-vivo image, or the like.

Figure 3:
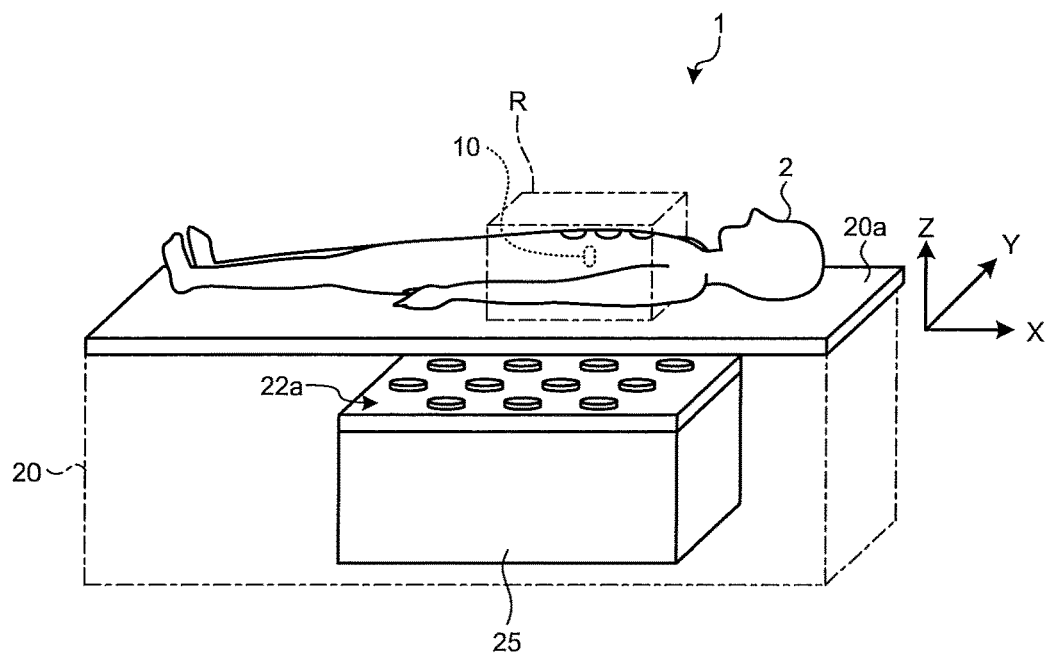
FIG. 3 is a schematic diagram illustrating an exemplary configuration of an exterior view of a guidance apparatus illustrated in FIG. 1.

FIG. 3 is a schematic diagram illustrating an exemplary configuration of an exterior view of a guidance apparatus illustrated in FIG. 1. As illustrated in FIG. 3, the guidance apparatus 20 includes a bed 20a as a mounting table on which a subject 2 is placed. At least the magnetic field generator 25 that generates a magnetic field and a plurality of sense coils 22a for detecting a position detection magnetic field generated by the position detection magnetic field generator 19 are arranged below the bed 20a. As a detection target space R, a three-dimensional closed area including a range in which the capsule endoscope 10 can move within the subject 2 (that is, a range of an observation target organ) is set in advance.

The reception unit 21 includes a plurality of receiving antennas 21a, and sequentially receives radio signals from the capsule endoscope 10 via the receiving antennas 21a. The reception unit 21 selects an antenna having the highest reception field strength from among the receiving antennas 21a and performs demodulation processing, or the like, on the radio signal from the capsule endoscope 10 received via the selected antenna, thereby extracting the image signal from the radio signal and outputting the image signal onto the display unit 23.

The plurality of sense coils 22a is arranged on a flat panel arranged parallel with the upper surface of the bed 20a. Each of the sense coils 22a is, for example, a cylindrical coil having a shape of a coil spring, and receives a magnetic field generated by the position detection magnetic field generator 19 of the capsule endoscope 10 and outputs a detection signal.

The position and posture detector 22 obtains a plurality of detection signals output from the plurality of sense coils 22a, and performs on these detection signals signal processing such as waveform shaping, amplification, A/D conversion, and FFT, thereby extracting the magnetic field information such as the amplitude and the phase of the position detection magnetic field. Furthermore, the position and posture detector 22 calculates the position and posture of the capsule endoscope 10 on the basis of the magnetic field information, and outputs the position and posture as position information.

The method of detecting the position and posture of the capsule endoscope 10 is not limited to the method using the above-described position detection magnetic field. For example, the position and posture of the capsule endoscope 10 may be detected on the basis of the distribution of the radio signal strength received by the reception unit 21. As an example, as disclosed in JP2007-283001 A, it is possible to obtain the position of the capsule endoscope 10 by repeating processing of appropriately setting an initial value of the position of the capsule endoscope 10 and calculating an estimated value of the position by the Gauss-Newton method until a deviation amount between the estimated value and the previous estimated value becomes a predetermined value or below.

The display unit 23 includes a screen formed with various displays such as a liquid crystal display, and displays an in-vivo image based on an image signal input from the reception unit 21, position information of the capsule endoscope 10, and various types of other information on the screen.

The operation input device 24 inputs operation input information into the controller 26 in accordance with operation performed from outside by the user. The operation input device 24 includes a target position and posture input unit 24a that receives an input of a target position and target posture, that is, instruction information for controlling the position and posture of the capsule endoscope 10. The operation input device 24 is constituted with an operation console including a joystick, various buttons and various switches, an input device such as a keyboard, or the like.

The magnetic field generator 25 generates a magnetic field that guides the capsule medical apparatus by acting on the permanent magnet 18 provided in the capsule endoscope 10. Specifically, the magnetic field generator 25 generates a magnetic field for relatively changing the position, an inclination angle, and an azimuth angle of the capsule endoscope 10 introduced into the subject 2, with respect to the subject 2. The magnetic field generator 25 includes an external permanent magnet 25a that generates a magnetic field, a planar position changing unit 25b, a vertical position changing unit 25c, an elevation angle changing unit 25d, and a pivot angle changing unit 25e, for changing the position and posture of the external permanent magnet 25a.

Figure 4:
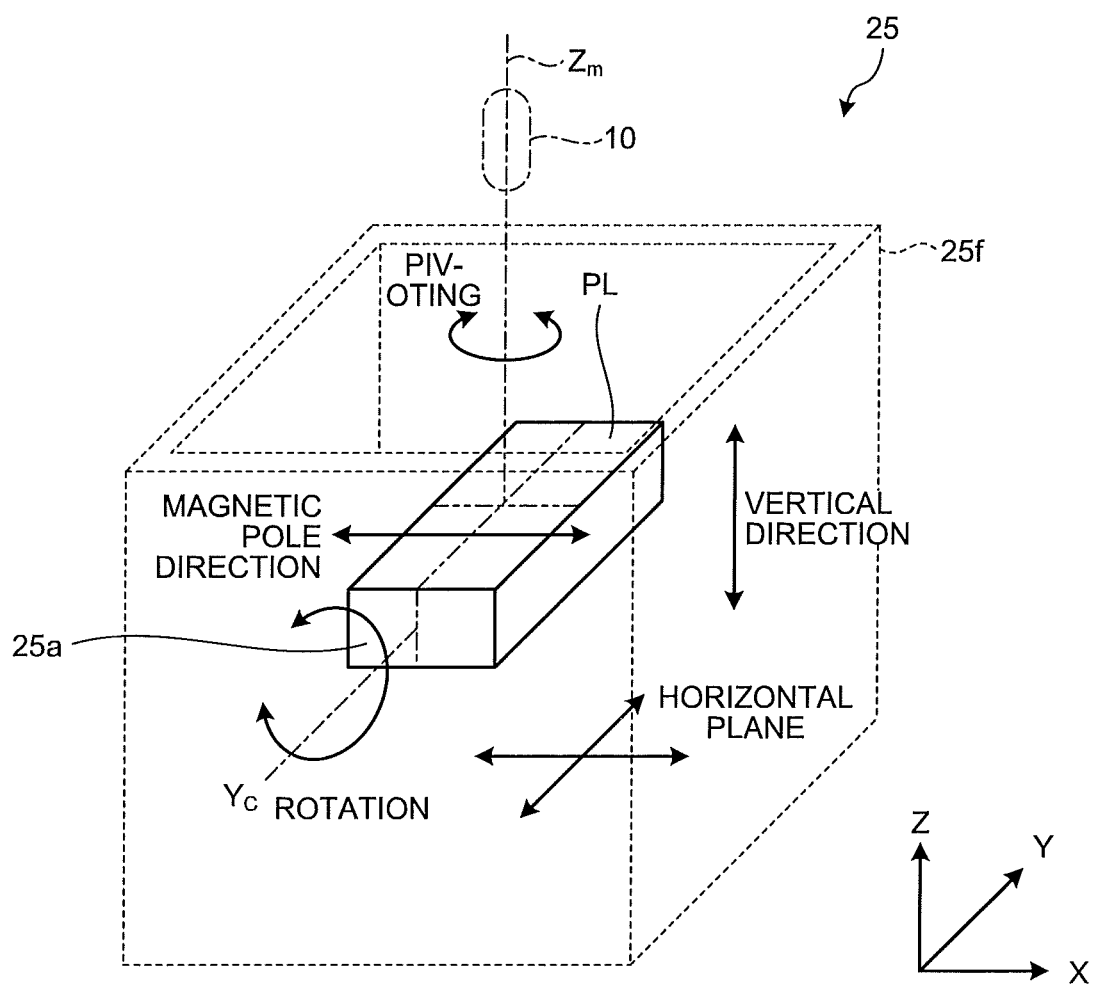
FIG. 4 is a schematic diagram for explaining an installation state of an external permanent magnet illustrated in FIG. 1.

FIG. 4 is a schematic diagram for explaining the installation state of the external permanent magnet illustrated in FIG. 1. As illustrated in FIG. 4, the external permanent magnet 25a is constituted with a bar magnet having a rectangular parallelepiped shape, for example. In an initial state, the external permanent magnet 25a is arranged such that one of four planes parallel to its magnetic pole direction is parallel with a horizontal plane (XY plane), that is, a plane orthogonal to the gravity direction. Hereinafter, arrangement of the external permanent magnet 25a when the external permanent magnet 25a is in the initial state will be referred to as a reference arrangement. Moreover, a surface of one of four surfaces parallel with the magnetic pole direction of oneself and opposed to the capsule endoscope 10 is also referred to as a capsule facing surface PL. In the following description, a direction in a plane orthogonal to the gravity direction will be referred to as a horizontal direction, the gravity direction will be referred to as a vertical direction, an angle to the plane orthogonal to the gravity direction will be referred to as an elevation angle, and an angle within the plane orthogonal to the gravity direction will be referred to as a pivot angle.

The planar position changing unit 25b translates the external permanent magnet 25a in a horizontal plane. That is, the external permanent magnet 25a is moved within the horizontal plane while the relative positions of two magnetic poles magnetized on the external permanent magnet 25a being maintained.

The vertical position changing unit 25c is a translation mechanism that translates the external permanent magnet 25a in the vertical direction (Z direction). That is, the external permanent magnet 25a is moved in the vertical direction while the relative positions of two magnetic poles magnetized on the external permanent magnet 25a being maintained.

The elevation angle changing unit 25d is a rotation mechanism that changes the magnetic pole direction angle with respect to the horizontal plane by rotating the external permanent magnet 25a within the vertical plane including the magnetic pole direction, on the external permanent magnet 25a. In other words, the elevation angle changing unit 25d rotates the external permanent magnet 25a with respect to an axis $Y_C$ in Y direction, that is parallel with the capsule facing surface PL and orthogonal to the magnetic pole direction and passes through the center of the external permanent magnet 25a. Hereinafter, the angle between the external permanent magnet 25a and the horizontal plane will be referred to as the elevation angle.

The pivot angle changing unit 25e pivots the external permanent magnet 25a around a vertical axis $Z_m$ passing through the center of the external permanent magnet 25a. Hereinafter, the rotational motion of the external permanent magnet 25a with respect to the vertical axis $Z_m$ will be referred to as a pivot motion. Moreover, the angle at which the external permanent magnet 25a pivots with respect to the reference arrangement will be referred to as a pivot angle.

Moreover, a ferromagnetic material 25f is arranged around the external permanent magnet 25a. The ferromagnetic material 25f functions as a magnetic field shielding material for shielding and weakening the magnetic field generated by the external permanent magnet 25a. The ferromagnetic material 25f is arranged in each of directions including the bottom surface except for the direction in which the external permanent magnet 25a faces the subject 2, and reduces the influence of the magnetic field generated by the external permanent magnet 25a on various devices and users such as doctors. The ferromagnetic material 25f on each of the surfaces may have a flat plate shape or may have a hole in a hand portion on a flat plate. In addition, the ferromagnetic material 25f may have a recess and irregularities formed therein for reinforcement and for enhancement of the shield property of the magnetic field. Note that it is sufficient that the ferromagnetic material 25f is arranged in at least one direction. For example, only two surfaces of the ferromagnetic material 25f may be arranged so as to face each other across the external permanent magnet 25a in the longitudinal direction of the bed 20a.

The controller 26 controls the operation of each of the components of the magnetic field generator 25 on the basis of the position information of the capsule endoscope 10 input from the position and posture detector 22 and the operation input information input from the operation input device 24. With this control, the controller 26 changes the relative position between the external permanent magnet 25a and the subject 2, the distance between the external permanent magnet 25a and the capsule endoscope 10, the rotation angle from the reference arrangement of the external permanent magnet 25a, that is, the elevation angle and the pivot angle, thereby guiding the capsule endoscope 10. At this time, the magnetic field generated by the external permanent magnet 25a might be distorted by the ferromagnetic material 25f and the capsule endoscope 10 cannot be guided to the target position and the target posture in some cases. To cope with this, the controller 26 controls the external permanent magnet 25a so as to generate a magnetic field that has been corrected so as to offset or reduce the deviation from the target position and the target posture of the capsule endoscope 10 due to the ferromagnetic material 25f. Specifically, the target position includes a target horizontal position and a target vertical position. Accordingly, the planar position changing unit 25b controls the external permanent magnet 25a so as to move the capsule endoscope 10 to the target horizontal position and the vertical position changing unit 25c controls the external permanent magnet 25a so as to move the capsule endoscope 10 to the target vertical position. The target posture includes a target elevation angle and a target pivot angle. Accordingly, the elevation angle changing unit 25d controls the external permanent magnet 25a such that the capsule endoscope 10 comes at the target elevation angle, and the pivot angle changing unit 25e controls the external permanent magnet 25a such that the capsule endoscope 10 comes at the target pivot angle. Note that these controls are executed by the controller 26 reading information used for control from a database of the storage unit 27 in accordance with the target position and target posture of the capsule endoscope 10.

As an example, the target position includes the target horizontal position and the target vertical position, and the planar position changing unit 25b performs correction control of the external permanent magnet 25a so as to offset or reduce the deviation of the capsule endoscope 10 from the target horizontal position due to the ferromagnetic material 25f and moves the capsule endoscope 10 to the target horizontal position. As another example, the vertical position changing unit 25c performs correction control on the external permanent magnet 25a so as to offset or reduce the decrease in the magnetic force acting on the capsule endoscope 10 due to the ferromagnetic material 25f, and moves the capsule endoscope 10 to the target vertical position. As another example, the target posture is constituted with the target elevation angle and the target pivot angle. In this case, the elevation angle changing unit 25d moves the capsule endoscope 10 to the target elevation angle by performing correction control of the external permanent magnet 25a so as to offset or reduce the deviation from the target elevation angle of the capsule endoscope 10 due to the ferromagnetic material 25f. As another example, the pivot angle changing unit 25e performs correction control on the external permanent magnet 25a so as to offset or reduce the deviation of the capsule endoscope 10 from the target pivot angle due to the ferromagnetic material 25f, and moves the capsule endoscope 10 to the target pivot angle.

As a further modification, it is allowable to move the capsule endoscope 10 to the target horizontal position so as to offset or reduce the deviation of the capsule endoscope 10 from the target horizontal position due to the ferromagnetic material 25f by using any one of the planar position changing unit 25b, the vertical position changing unit 25c, the elevation angle changing unit 25d, and the pivot angle changing unit 25e, or by using two or more of them in combination. That is, for example, the controller 26 performs correction control of the planar position changing unit 25b, the vertical position changing unit 25c, the elevation angle changing unit 25d, and the pivot angle changing unit 25e so as to offset or reduce the deviation of the capsule endoscope 10 from the target horizontal position due to the ferromagnetic material 25f, thereby controlling the horizontal position, the vertical position, the elevation angle, and the pivot angle of the external permanent magnet 25a so as to move the capsule endoscope 10 to the target horizontal position.

Similarly, it is allowable to move the capsule endoscope 10 to the target horizontal position, target elevation angle, or target pivot angle so as to offset or reduce the deviation of the capsule endoscope 10 from the target vertical position, target elevation angle, or target pivot angle due to the ferromagnetic material 25f by using any one of the planar position changing unit 25b, the vertical position changing unit 25c, the elevation angle changing unit 25d, and the pivot angle changing unit 25e, or by using two or more of them in combination. That is, for example, the controller 26 performs correction control of the elevation angle changing unit 25d, and the pivot angle changing unit 25e so as to offset or reduce the deviation of the capsule endoscope 10 from the target elevation angle due to the ferromagnetic material 25f, thereby controlling the elevation angle and the pivot angle of the external permanent magnet 25a so as to move the capsule endoscope 10 to the target elevation angle. Note that a specific example of the control of the controller 26 will be described in detail in each of Examples to be described below.

The storage unit 27 is configured with a storage medium that rewritably stores information, such as a flash memory or a hard disk, and with a writing/reading apparatus that writes and reads information on the storage medium. In addition to the image data of an in-vivo image group of the subject 2 captured by the capsule endoscope 10, the storage unit 27 stores information including various programs and parameters used by the controller 26 to control each of the components of the guidance apparatus 20.

Figure 5:
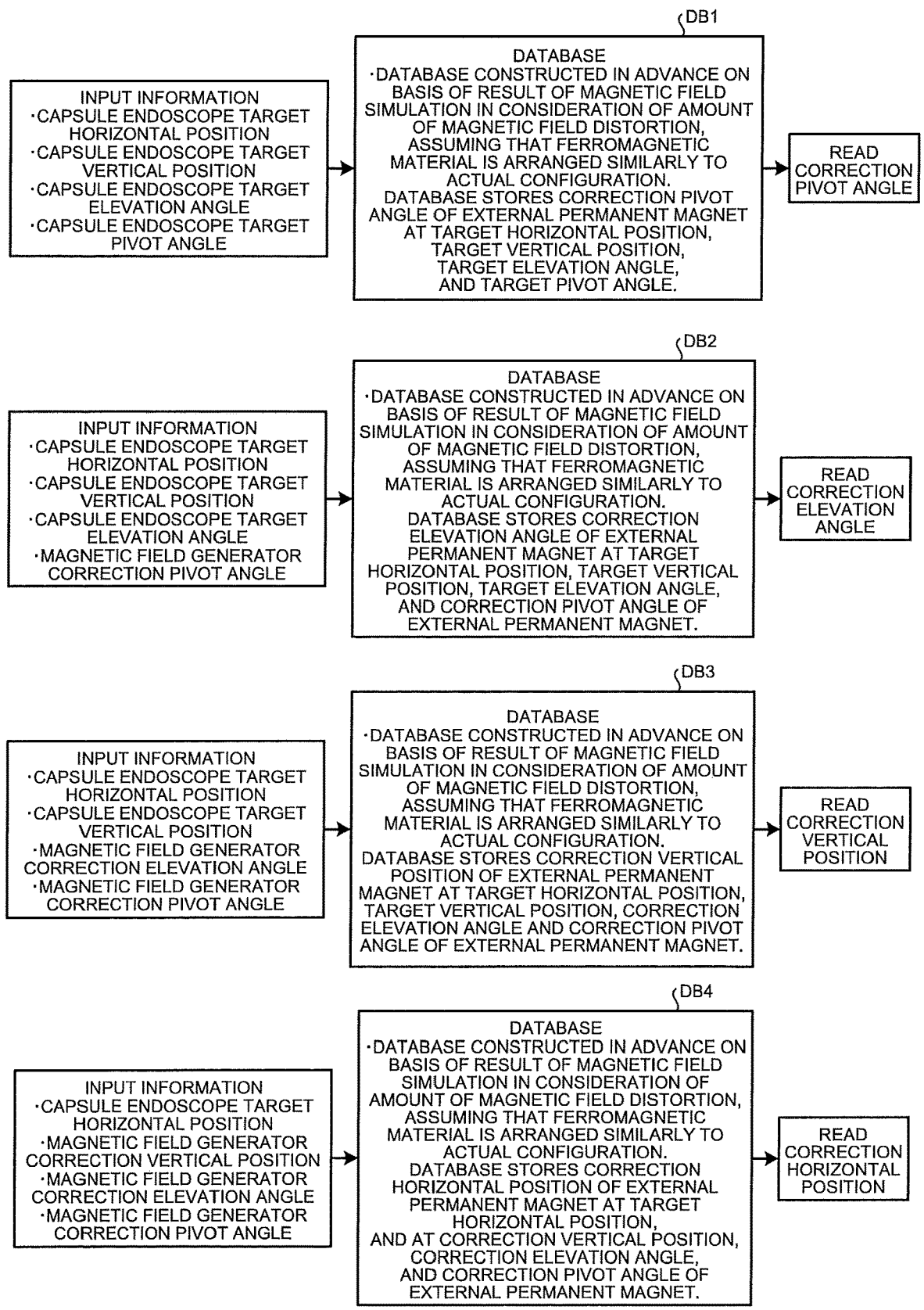
FIG. 5 is a diagram illustrating an exemplary method for correcting the position and posture of the external permanent magnet using a database of a storage unit.

The storage unit 27 further holds, as a database, the degree of deviation in the position in the horizontal direction and the position in the vertical direction, the elevation angle, and the pivot angle of the capsule endoscope 10 due to the influence of the ferromagnetic material 25f. FIG. 5 is a diagram illustrating an exemplary method for correcting the position and posture of the external permanent magnet 25a using the database of the storage unit. As illustrated in FIG. 5, the storage unit 27 includes databases DB1 to DB4, for example. The databases DB1 to DB4 are databases constructed in advance on the basis of a result of magnetic field simulation in consideration of the amount of magnetic field distortion, assuming that ferromagnetic materials 25f are arranged similarly to the actual configuration. In accordance with the input information, the controller 26 reads information used for control from the databases DB1 to DB4 of the storage unit 27 as appropriate.

The database DB1 is a database that stores a correction pivot angle as the pivot angle of the external permanent magnet 25a that offsets or reduces the deviation of the pivot angle of the capsule endoscope 10 from the target pivot angle due to the ferromagnetic material 25f in a case where the capsule endoscope 10 is at the target horizontal position, the target vertical position, the target elevation angle, and the target pivot angle.

The database DB2 is a database that stores a correction elevation angle as the elevation angle of the external permanent magnet 25a that offsets or reduces the deviation of the elevation angle of the capsule endoscope 10 from the target elevation angle due to the ferromagnetic material 25f in a case where the capsule endoscope 10 is at the target horizontal position, the target vertical position, the target elevation angle, and the external permanent magnet 25a is at the correction pivot angle (that is, the pivot angle of the external permanent magnet 25a matches the correction pivot angle).

The database DB3 is a database that stores a correction vertical position as the vertical position of the external permanent magnet 25a that offsets or reduces the deviation of the vertical position of the capsule endoscope 10 from the target vertical position due to the ferromagnetic material 25f in a case where the capsule endoscope 10 is at the target horizontal position and the target vertical position, and where the external permanent magnet 25a is at the correction elevation angle and the correction pivot angle.

The database DB4 is a database that stores a correction horizontal position as the horizontal position of the external permanent magnet 25a that offsets or reduces the deviation of the horizontal position of the capsule endoscope 10 from the target horizontal position by the ferromagnetic material 25*f* in a case where the capsule endoscope 10 is at the target horizontal position and where the external permanent magnet 25*a* is at the correction vertical position, the correction elevation angle and the correction pivot angle. Note that these databases may be constructed in advance by actually measuring the influence of the ferromagnetic material 25*f* on the position or posture of the capsule endoscope 10.

As described above, when guiding the capsule endoscope 10 to the target position and the target posture, the guidance apparatus 20 according to the present embodiment causes the external permanent magnet 25*a* to generate a magnetic field that has been corrected to offset or reduce the influence of the ferromagnetic material 25*f* on the position or posture of the capsule endoscope 10. As a result, the guidance apparatus 20 is a guidance apparatus having a ferromagnetic material 25*f* and capable of guiding the capsule medical apparatus to a target position and posture.

Figure 6:
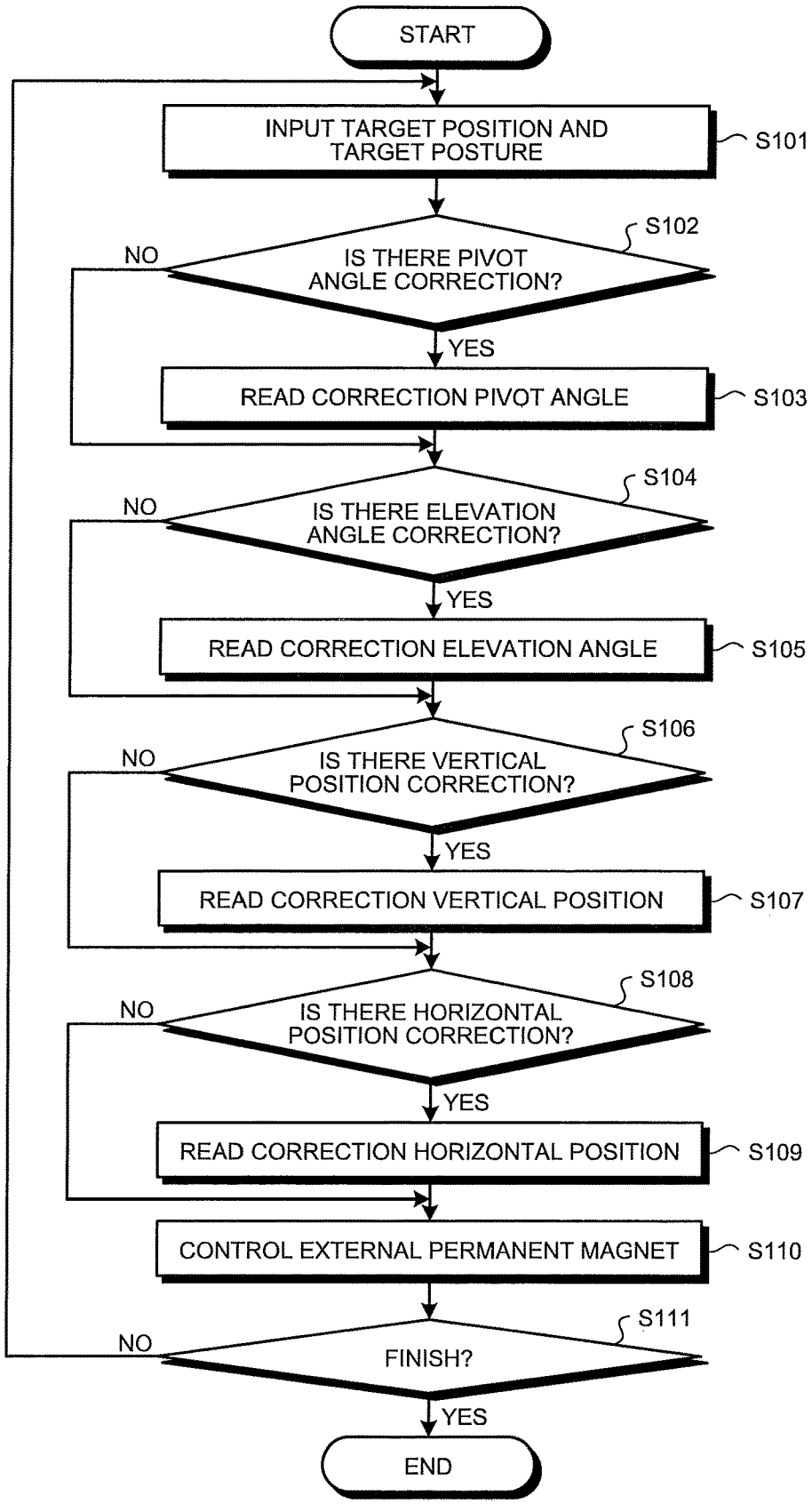
FIG. 6 is a flowchart illustrating operation of the capsule medical apparatus guidance system illustrated in FIG. 1.

Next, operation of the capsule medical apparatus guidance system 1 will be described. FIG. 6 is a flowchart illustrating the operation of the capsule medical apparatus guidance system illustrated in FIG. 1.

When the capsule medical apparatus guidance system 1 starts guiding the capsule endoscope 10, the user first inputs a target position and a target posture from the target position and posture input unit 24*a* of the operation input device 24 (step S101). The target position and posture input unit 24*a* that has received the input of the target position (target horizontal position and target vertical position) and the target posture (target elevation angle and target pivot angle) outputs a predetermined control signal to the controller 26.

First, the controller 26 determines whether to correct the pivot angle of the external permanent magnet 25*a* (step S102). In a case where it is determined by the controller 26 to correct the pivot angle (step S102: Yes), the controller 26 reads the correction pivot angle from the database DB1 as illustrated in FIG. 5 (step S103). In contrast, in a case where it is determined by the controller 26 not to correct that the pivot angle (step S102: No), the correction pivot angle is not read and the processing proceeds to the next step.

Subsequently, the controller 26 determines whether to correct the elevation angle of the external permanent magnet 25*a* (step S104). In a case where it is determined by the controller 26 to correct the elevation angle (step S104: Yes), the controller 26 reads the correction elevation angle from the database DB2 as illustrated in FIG. 5 (step S105). In contrast, in a case where it is determined by the controller 26 not to correct the elevation angle (step S104: No), the correction elevation angle is not read and the processing proceeds to the next step.

Furthermore, the controller 26 determines whether to correct the vertical position of the external permanent magnet 25*a* (step S106). In a case where it is determined by the controller 26 to correct the vertical position (step S106: Yes), the controller 26 reads the correction vertical position from the database DB3 as illustrated in FIG. 5 (step S107). In contrast, in a case where it is determined by the controller 26 not to correct the vertical position (step S106: No), the correction vertical position is not read and the processing proceeds to the next step.

Subsequently, the controller 26 determines whether to correct the horizontal position of the external permanent magnet 25*a* (step S108). In a case where it is determined by the controller 26 to correct the horizontal position (step S108: Yes), the controller 26 reads the correction horizontal position from the database DB4 as illustrated in FIG. 5 (step S109). In contrast, in a case where it is determined by the controller 26 not to correct the horizontal position (step S108: No), the correction horizontal position is not read and the processing proceeds to the next step.

Thereafter, the controller 26 controls the planar position changing unit 25*b*, the vertical position changing unit 25*c*, the elevation angle changing unit 25*d*, and the pivot angle changing unit 25*e* such that the external permanent magnet 25*a* is arranged at the correction horizontal position, the correction vertical position, the correction elevation angle, and the correction pivot angle (step S110). Then, in a case where the capsule medical apparatus guidance system 1 has performed a predetermined input for finishing the guidance of the capsule endoscope 10 (step S111: Yes), the operation of the capsule medical apparatus guidance system 1 is finished. In contrast, in a case where the capsule medical apparatus guidance system 1 has not performed a predetermined input for finishing the guidance of the capsule endoscope 10 (step S111: No), the processing returns to step S101 and the operation is continued.

Note that, in the above-described control flow, the input of the target position and the target posture into the target position and posture input unit 24*a* of the operation input device 24 is performed by a joystick, for example. The state in which the joystick is continuously inclined in a predetermined direction corresponds to the state of inputting a target position separated by a predetermined distance from the position of the capsule endoscope 10 at that time, or inputting a target posture obtained by changing a predetermined angle. During this time, the capsule endoscope 10 moves at a constant speed in a direction of inclination of the joystick. Moreover, in the control flow described above, the input of the target position and the target posture into the target position and posture input unit 24*a* of the operation input device 24 may be performed by clicking a position on the display unit 23 using a mouse. In this case, the input of the target position is performed once, and the above-described control flow is executed once.

Moreover, in the above-described control flow, the correction pivot angle, the correction elevation angle, the correction vertical position, and the correction horizontal position are calculated in this order, but the order of calculation is not particularly limited. For example, it may be configured to calculate the correction elevation angle and then calculate the correction pivot angle. For example, it may be configured to calculate the correction horizontal position and then calculate the correction vertical position.

While in the above-described control flow, control is performed so as to correct all values of the position in the horizontal direction, the position in the vertical direction, the elevation angle, and the pivot angle of the external permanent magnet 25*a*, the disclosure is not limited to this. It is allowable to have a configuration to perform correction using any one of the position in the horizontal direction, the position in the vertical direction, the elevation angle, and the pivot angle of the external permanent magnet 25*a* or some of them in combination, and not perform correction for the other values.

In the control flow described above, the deviation from the target pivot angle of the capsule endoscope 10 is corrected by the pivot angle of the external permanent magnet 25*a*, and the deviation from the target elevation angle of the capsule endoscope 10 is corrected by the elevation angle of the external permanent magnet 25*a*, the deviation from the target vertical position of the capsule endoscope 10 is corrected by the vertical position of the external permanent magnet 25*a*, and the deviation of the capsule endoscope 10 from the target horizontal position is corrected by the horizontal position of the external permanent magnet 25a. The configuration, however, is not limited to this. For example, it is allowable to have a configuration, in which, in a case where the target horizontal position of the capsule endoscope 10 alone is input and the capsule endoscope 10 is moved in the horizontal direction, the deviation of the capsule endoscope 10 from the target horizontal position is corrected by the pivot angle, elevation angle, and the horizontal position of the external permanent magnet 25a. Similarly, it is allowable to have a configuration, in which, in a case where the target elevation angle of the capsule endoscope 10 alone is input and the elevation angle of the capsule endoscope 10 alone is to be changed, the deviation of the capsule endoscope 10 from the target elevation angle is appropriately corrected by the pivot angle and the elevation angle of the external permanent magnet 25a. Furthermore, for example, it is allowable to have a configuration in which the deviations of the target horizontal position and the target elevation angle of the capsule endoscope 10 are corrected solely by the elevation angle of the external permanent magnet 25a.

Moreover, while in the above-described control flow, the controller 26 reads the correction horizontal position, the correction vertical position, the correction elevation angle, and the correction pivot angle from the storage unit 27, the disclosure is not limited to this. For example, it is allowable to configure such that the controller 26 reads a deviation amount from the target position and the target posture of the capsule endoscope 10 due to the influence of the ferromagnetic material 25f from the storage unit 27, and the controller 26 calculates the correction horizontal position, the correction vertical position, the correction elevation angle, and the correction pivot angle.

Example 1

Figure 7:
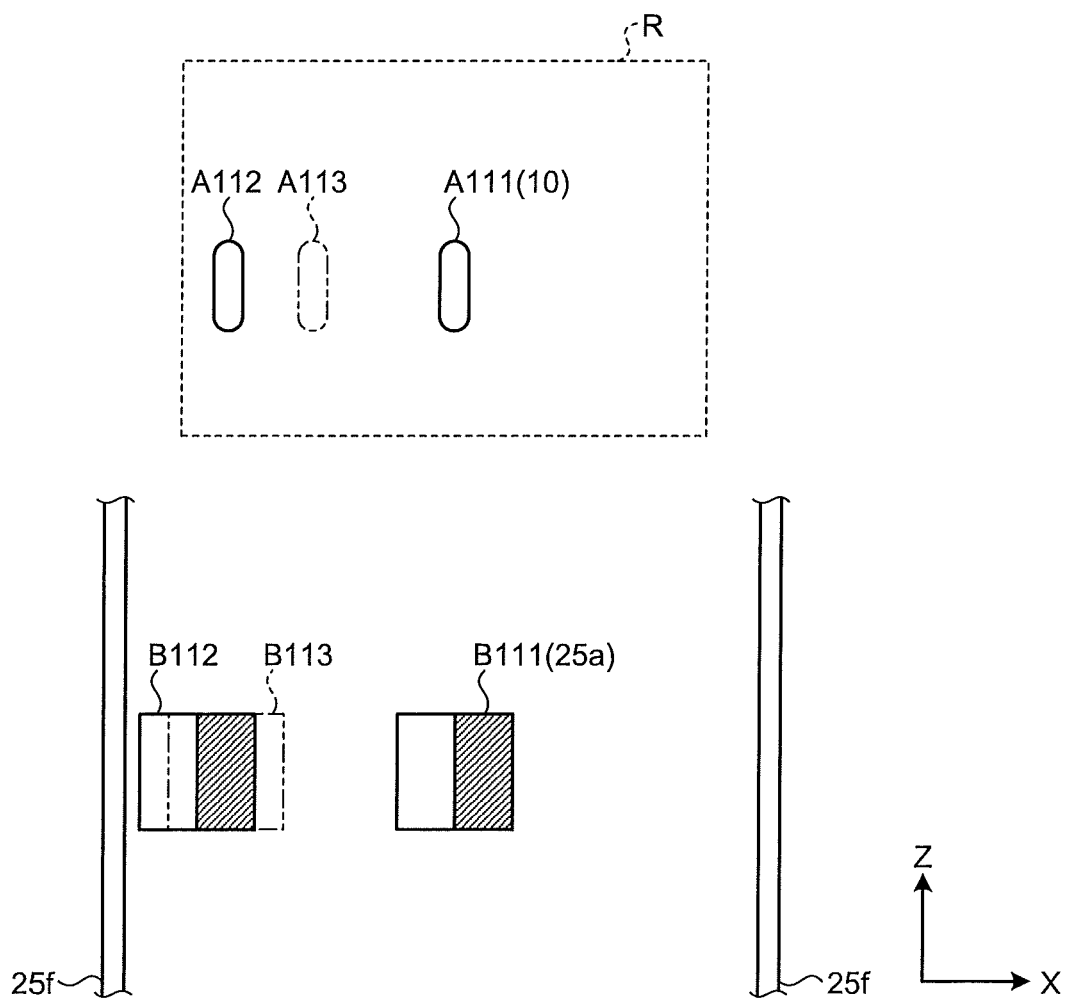
FIG. 7 is a diagram for explaining a method for controlling the external permanent magnet of the guidance apparatus according to Example 1.

Next, a method for controlling the external permanent magnet 25a by the controller 26 of the guidance apparatus 20 according to Example 1 will be described. FIG. 7 is a diagram for explaining a method for controlling the external permanent magnet of the guidance apparatus according to Example 1. Hereinafter, in the following description, as illustrated in FIG. 7, the position of the capsule endoscope 10 will be represented by a capsule position A111, or the like, and the position of external permanent magnet 25a will be represented by a magnet position B111, or the like. At that time, the reference signs of the capsule endoscope 10 and the external permanent magnet 25a will be appropriately omitted.

As illustrated in FIG. 7, in the guidance apparatus 20 according to Example 1 corrects the position of the external permanent magnet 25a in the horizontal direction so as to offset or reduce the influence of the ferromagnetic material 25f on the horizontal position of the capsule endoscope 10. Specifically, in the case of moving the capsule endoscope 10 from the capsule position A111 to a capsule position A112 as a target position (moving in the horizontal direction), the external permanent magnet 25a is moved from the magnet position B111 to a magnet position B112 that has been corrected to offset or reduce the influence of the ferromagnetic material 25f (positional deviation in horizontal direction).

That is, in the guidance apparatus 20, in a case where the external permanent magnet 25a and the ferromagnetic material 25f are brought closer to each other and the influence of the ferromagnetic material 25f is increased when the target position of the capsule endoscope 10 in the horizontal direction is brought closer to the ferromagnetic material 25f, the external permanent magnet 25a is brought closer to the ferromagnetic material 25f in the horizontal direction than the capsule endoscope 10.

Next, operation of the guidance apparatus 20 according to Example 1 will be described. First, it is assumed that the capsule endoscope 10 is moved from the capsule position A111 to the capsule position A112, that is, the target horizontal position. At this time, unless the influence of the ferromagnetic material 25f is taken into consideration, the external permanent magnet 25a would be moved from the magnet position B111 to the magnet position B113. In this case, however, due to the influence of the ferromagnetic material 25f, the position of the actual capsule endoscope 10 deviates in the horizontal direction to be located at the capsule position A113. The correction horizontal position (magnet position B112) of the external permanent magnet 25a for correcting the deviation amount for the position in the horizontal direction is recorded in advance in the database of the storage unit 27. Accordingly, the controller 26 reads the correction horizontal position from the storage unit 27 and controls the planar position changing unit 25b and moves the external permanent magnet 25a from the magnet position B111 to the magnet position B112. As a result, the capsule endoscope 10 moves from the capsule position A111 to the capsule position A112.

As illustrated in Example 1, there might be a case where the magnetic field is distorted by the ferromagnetic material 25f with the movement of the capsule endoscope 10 in the horizontal direction, leading to deviation of the position of the capsule endoscope 10 in the horizontal direction. In this case, by correcting the position of the external permanent magnet 25a in the horizontal direction, it is possible to guide the capsule endoscope 10 to the target position.

In this manner, it is possible to correct the positional deviation in the horizontal direction by increasing the moving amount of the external permanent magnet 25a toward the ferromagnetic material 25f with the increase of the influence of the ferromagnetic material 25f.

Example 2

Figure 8:
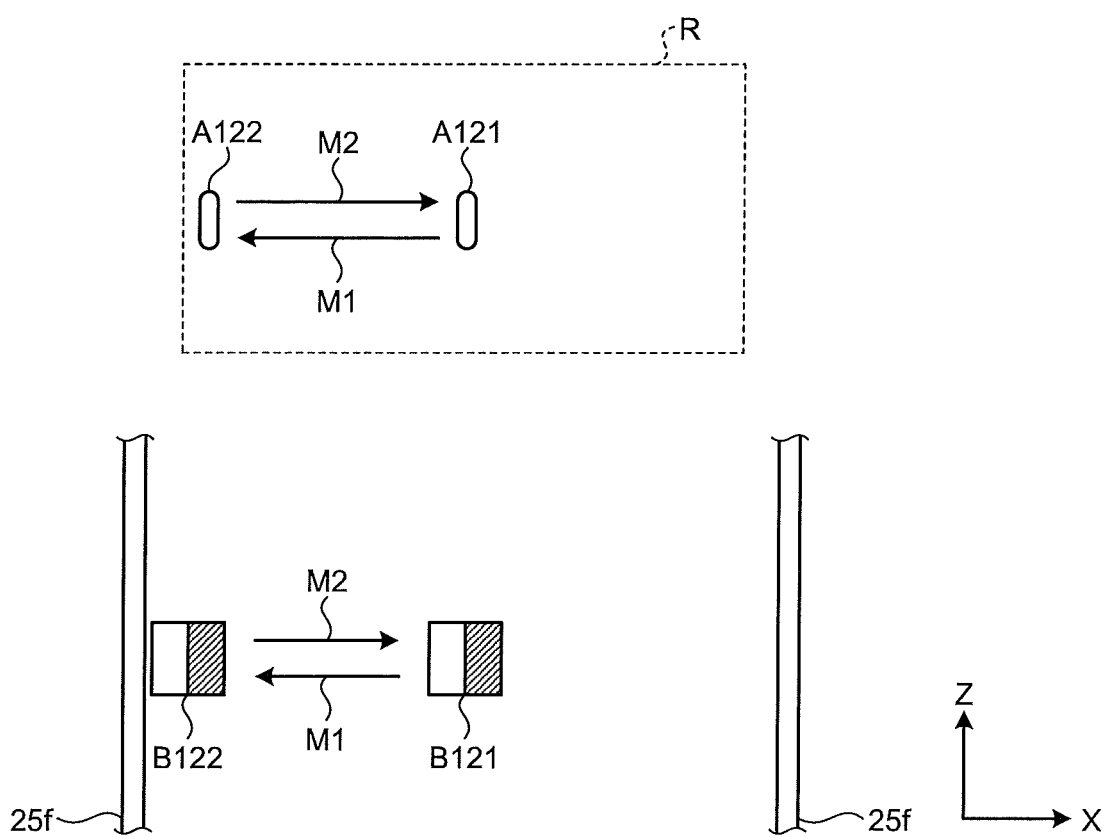
FIG. 8 is a diagram for explaining a method for controlling an external permanent magnet of a guidance apparatus according to Example 2.
Figure 9:
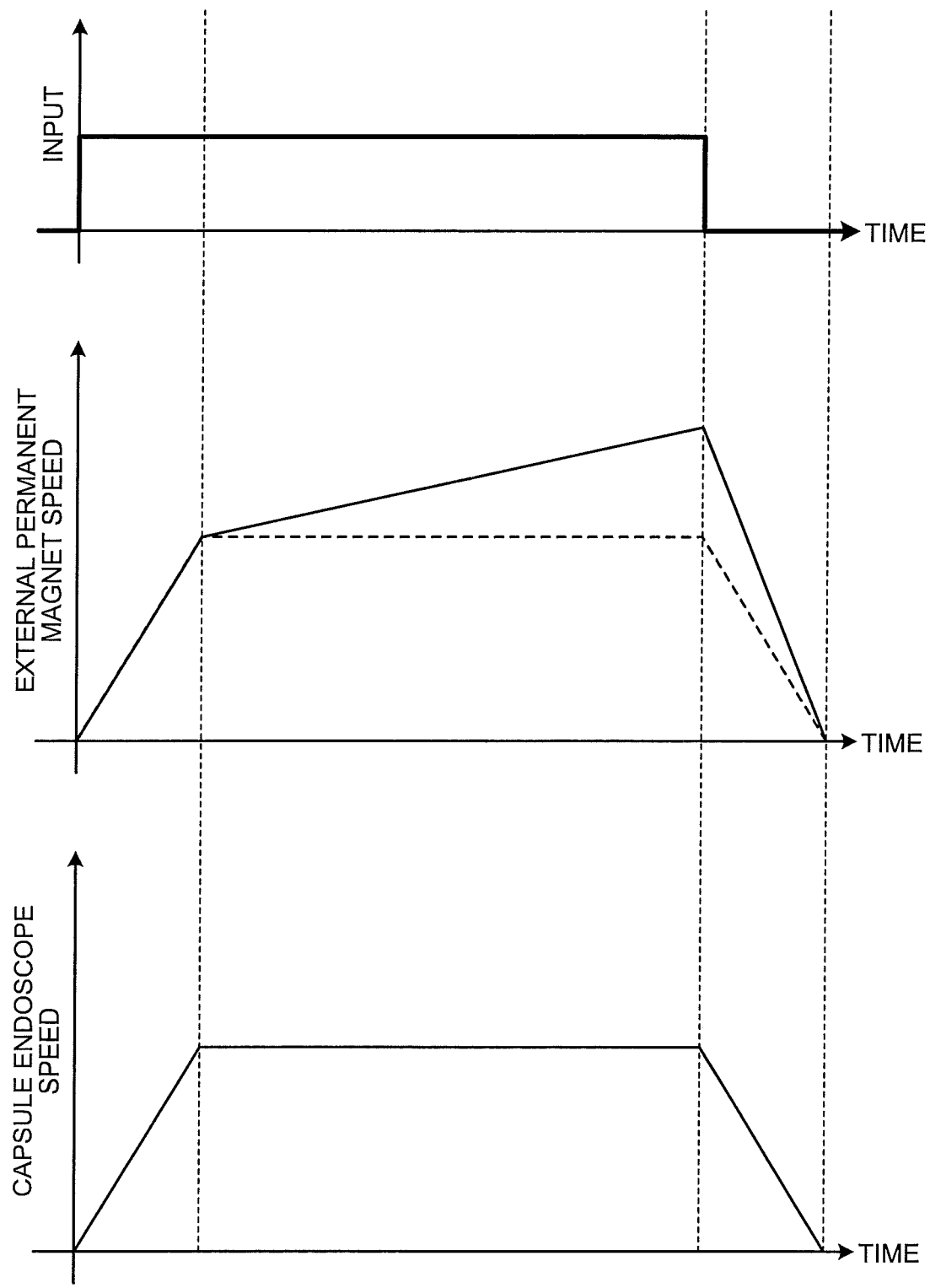
FIG. 9 is a diagram illustrating a relationship between an input into a target position and posture input unit, the speed of the external permanent magnet, and the speed of the capsule endoscope in Example 2.
Figure 10:
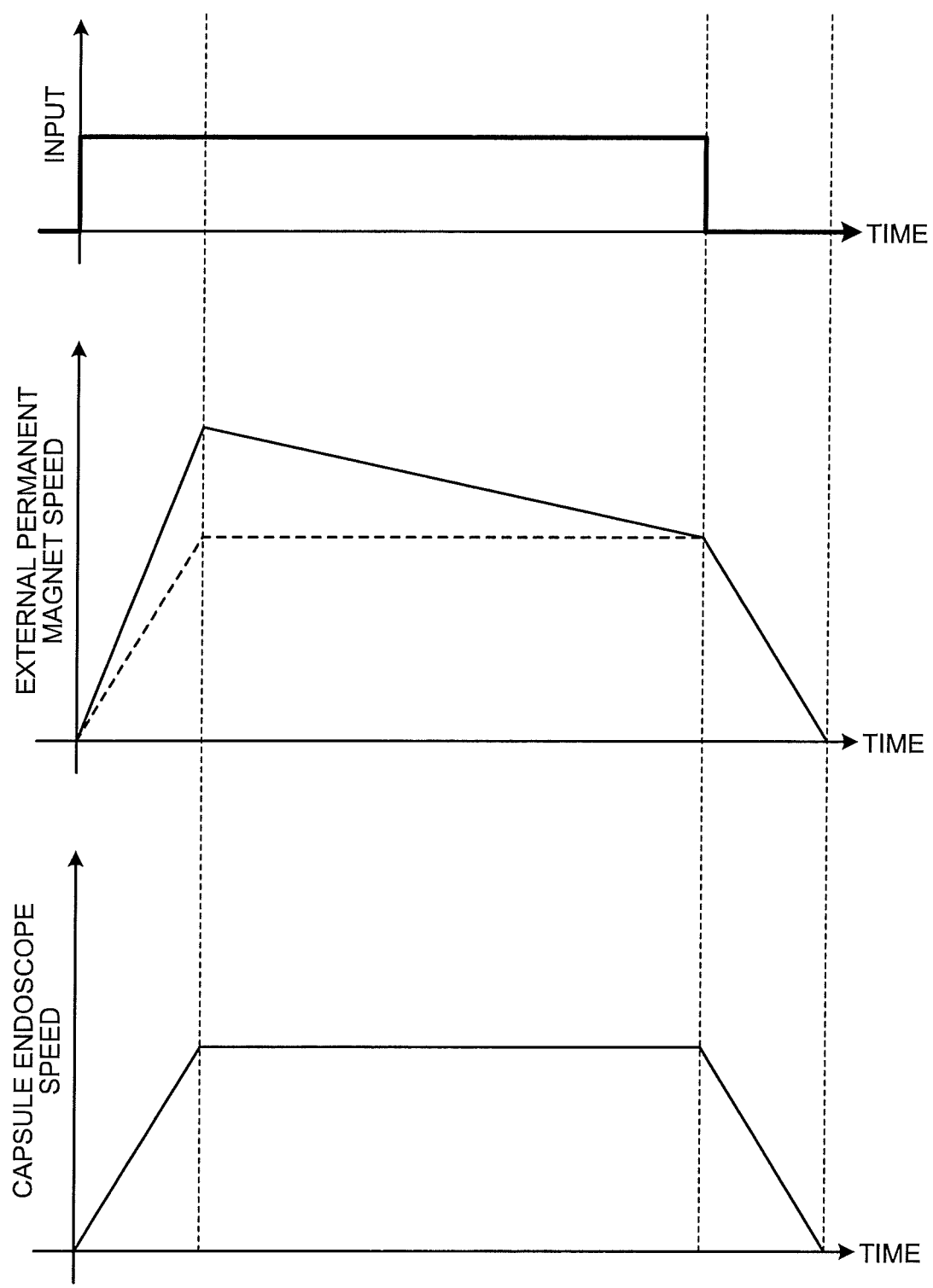
FIG. 10 is a diagram illustrating a relationship between the input into a target position and posture input unit, the speed of the external permanent magnet, and the speed of the capsule endoscope in Example 2.

A method for controlling the external permanent magnet 25a by the controller 26 of the guidance apparatus 20 according to Example 2 will be described. FIG. 8 is a diagram for explaining a method for controlling the external permanent magnet of the guidance apparatus according to Example 2. As illustrated in FIG. 8, the guidance apparatus 20 according to Example 2 moves the external permanent magnet 25a between the magnet position B121 and the magnet position B122 in order to move the capsule endoscope 10 between a capsule position A121 and a capsule position A122. FIGS. 9 and 10 are diagrams illustrating a relationship between the input into a target position and posture input unit, the speed of the external permanent magnet, and the speed of the capsule endoscope in Example 2. FIG. 9 corresponds to movement M1 from the capsule position A121 to the capsule position A122, and FIG. 10 corresponds to movement M2 from the capsule position A122 to the capsule position A121.

First, in FIG. 9, a constant input is performed into the target position and posture input unit 24a in a direction of bringing the capsule endoscope 10 closer to the ferromagnetic material 25f (moving in the left direction in the page of FIG. 8). This corresponds to repeated inputs of the target horizontal position close to the ferromagnetic material 25f by a predetermined distance from the capsule endoscope 10.

At this time, similarly to the case of Example 1, the guidance apparatus 20 corrects the position of the external permanent magnet 25a in the horizontal direction so as to offset or reduce the influence of the ferromagnetic material 25f on the horizontal position of the capsule endoscope 10. That is, the guidance apparatus 20 moves the external permanent magnet 25a closer to the ferromagnetic material 25f (to the left in FIG. 8) by an amount to offset the influence of the ferromagnetic material 25f. Moreover, the closer the external permanent magnet 25a is to the ferromagnetic material 25f, the greater the correction amount of the external permanent magnet 25a when bringing the capsule endoscope 10 closer to the ferromagnetic material 25f. Accordingly, in a case where the capsule endoscope 10 is brought close to the ferromagnetic material 25f at a constant speed, the closer the capsule endoscope 10 is to the ferromagnetic material 25f, the higher the speed of the external permanent magnet 25a. This is because the closer the external permanent magnet 25a is to the ferromagnetic material 25f, the greater the influence of the ferromagnetic material 25f.

The speed from the point of the input of the target horizontal position is performed once until the point at which the capsule endoscope 10 is moved to the target horizontal position is set to a constant speed. Accordingly, as illustrated in FIG. 9, it is set such that the closer the capsule endoscope 10 to the ferromagnetic material 25f, the higher the speed of the external permanent magnet 25a.

Next, in FIG. 10, a constant input is performed into the target position and posture input unit 24a in a direction of bringing the capsule endoscope 10 away from the ferromagnetic material 25f (moving in the right direction in the page of FIG. 8). At this time, the control opposite to the control in FIG. 9 is performed. Accordingly, in a case where the capsule endoscope 10 is brought away from the ferromagnetic material 25f at a constant speed as illustrated in FIG. 10, it is set such that the farther the capsule endoscope 10 is from the ferromagnetic material 25f, the lower the speed of the external permanent magnet 25a.

As described above, in a case where the external permanent magnet 25a is brought closer to the ferromagnetic material 25f, the guidance apparatus 20 according to Example 2 moves the external permanent magnet 25a so as to be accelerated, and in a case where the external permanent magnet 25a is brought away from the ferromagnetic material 25f, the guidance apparatus 20 moves the external permanent magnet 25a so as to be decelerated. As a result, the user can operate the capsule endoscope 10 at a constant speed irrespective of the relative positions between the external permanent magnet 25a and the ferromagnetic material 25f, leading to good operability.

Example 3

Figure 11:
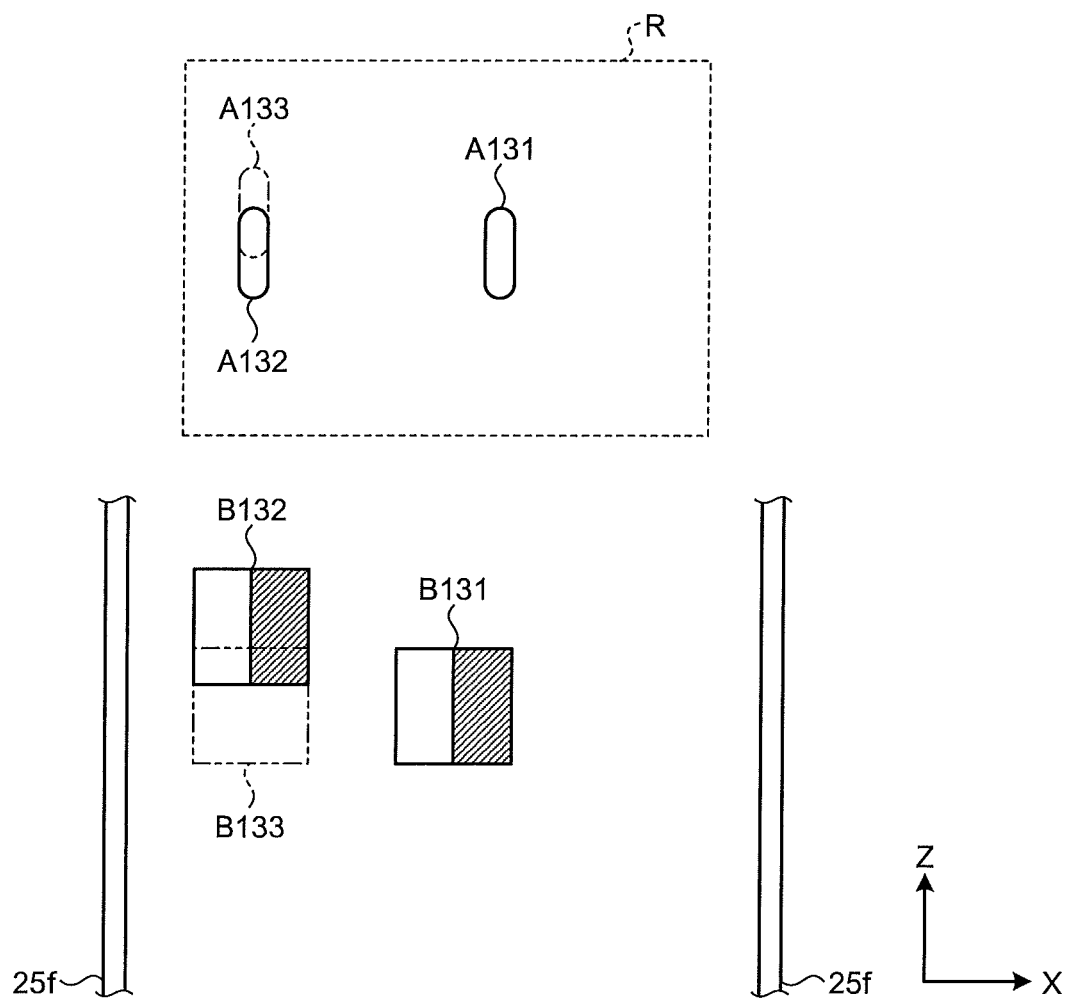
FIG. 11 is a diagram for explaining a method for controlling an external permanent magnet of a guidance apparatus according to Example 3.

A method for controlling the external permanent magnet 25a by the controller 26 of the guidance apparatus 20 according to Example 3 will be described. FIG. 11 is a diagram for explaining a method for controlling the external permanent magnet of the guidance apparatus according to Example 3. As illustrated in FIG. 11, the guidance apparatus 20 according to Example 3 corrects the position of the external permanent magnet 25a in the vertical direction so as to offset or reduce the influence of the ferromagnetic material 25f on the vertical position of the capsule endoscope 10. Specifically, in the case of moving the capsule endoscope 10 from a capsule position A131 to a capsule position A132 as a target position (moving in the horizontal direction), the external permanent magnet 25a is moved from the magnet position B131 to a magnet position B132 that has been corrected to offset or reduce the influence of the ferromagnetic material 25f (change in magnetic force).

That is, in the guidance apparatus 20, in a case where the external permanent magnet 25a and the ferromagnetic material 25f are brought closer to each other and the influence of the ferromagnetic material 25f is increased when the capsule endoscope 10 is brought closer to the ferromagnetic material 25f in the horizontal direction, the distance between the capsule endoscope 10 and the external permanent magnet 25a is decreased.

Next, operation of the guidance apparatus 20 according to Example 3 will be described. First, it is assumed that the capsule endoscope 10 is moved from the capsule position A131 to the capsule position A132, that is, the target position. At this time, unless the influence of the ferromagnetic material 25f is taken into consideration, the external permanent magnet 25a would be moved from the magnet position B131 to the magnet position B133. In this case, however, due to the influence of the ferromagnetic material 25f, the magnetic force acting on the capsule endoscope 10 decreases, and the actual position of the capsule endoscope 10 floats in the vertical direction (direction opposite to the gravity in the example of FIG. 11), to be located at a capsule position A133. The correction vertical position (magnet position B132) of the external permanent magnet 25a for correcting the change amount of the magnetic force in the vertical direction is recorded in advance in the database of the storage unit 27. Accordingly, the controller 26 reads the correction vertical position from the storage unit 27, controls the planar position changing unit 25b and the vertical position changing unit 25c, and moves the external permanent magnet 25a from the magnet position B131 to the magnet position B132. As a result, the capsule endoscope 10 moves from the capsule position A131 to the capsule position A132.

As illustrated in Example 3, the influence of the ferromagnetic material 25f on the vertical position of the capsule endoscope 10 changes with the movement of the capsule endoscope 10 in the horizontal direction. Accordingly, the capsule endoscope 10 might deviate in the vertical direction in some cases. In this case, by correcting the position of the external permanent magnet 25a in the vertical direction, it is possible to guide the capsule endoscope 10 to the target position.

Example 4

Figure 12:
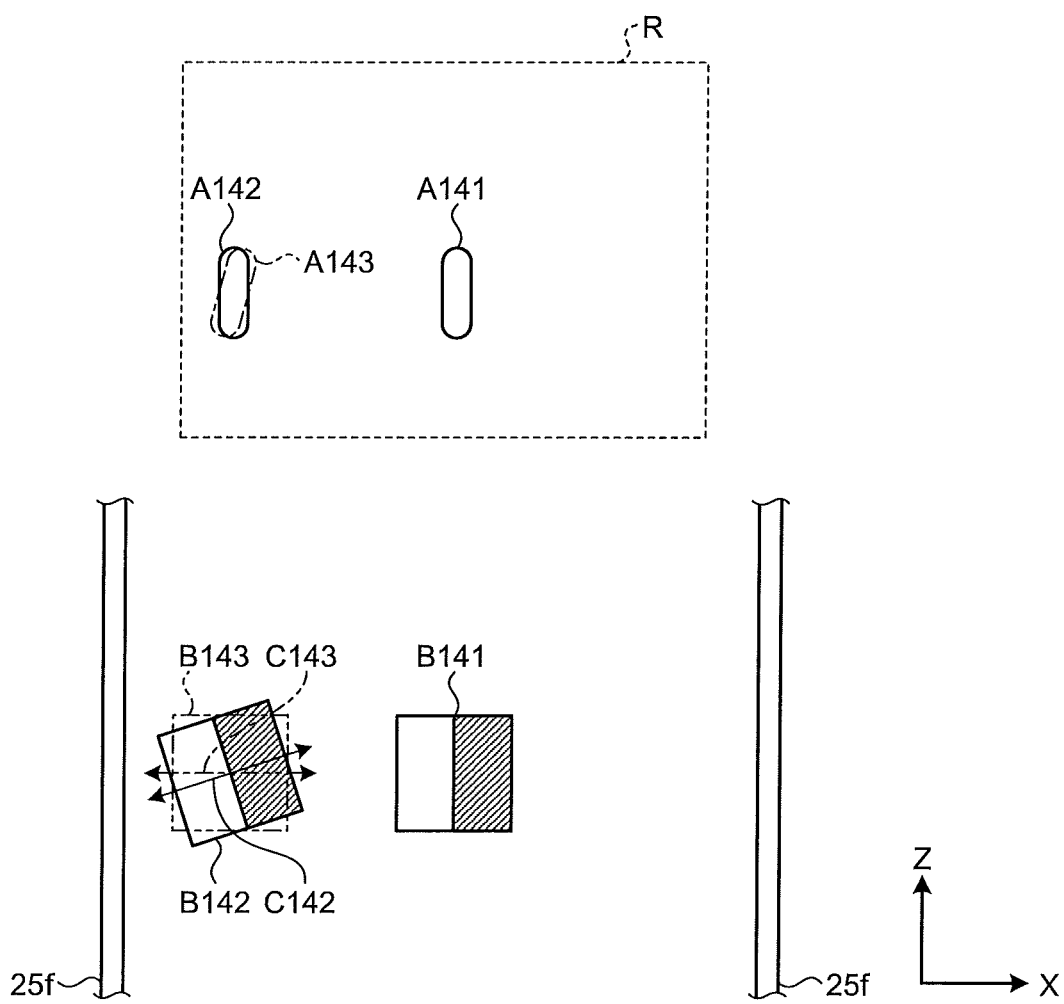
FIG. 12 is a diagram for explaining a method for controlling an external permanent magnet of a guidance apparatus according to Example 4.

A method for controlling the external permanent magnet 25a by the controller 26 of the guidance apparatus 20 according to Example 4 will be described. FIG. 12 is a diagram for explaining a method for controlling the external permanent magnet of the guidance apparatus according to Example 4. As illustrated in FIG. 12, the guidance apparatus 20 according to Example 4 corrects the elevation angle of the external permanent magnet 25a so as to offset or reduce the influence of the ferromagnetic material 25f on the elevation angle of the capsule endoscope 10. Specifically, in a case of moving the capsule endoscope 10 from a capsule position A141 to a capsule position A142 as a target position and target posture (moving in the horizontal direction), the external permanent magnet 25a is moved from a magnet position B141 to a magnet position B142 that has been corrected to offset or reduce the influence of the ferromagnetic material 25f (deviation in elevation angle).

That is, in the guidance apparatus 20, in a case where the external permanent magnet 25a and the ferromagnetic material 25f are brought closer to each other and the influence of the ferromagnetic material 25f is increased when the capsule endoscope 10 is guided to the target position and the target posture, the inclination of the magnetic pole direction of the external permanent magnet 25a with respect to the horizontal plane is increased. Specifically, the external permanent magnet 25a is rotated from a direction C143 to a direction C142 in the magnetic pole direction.

Next, operation of the guidance apparatus 20 according to Example 4 will be described. First, it is assumed that the capsule endoscope 10 is moved from the capsule position A141 to the capsule position A142, that is, the target position and the target posture. At this time, unless the influence of the ferromagnetic material 25f is taken into consideration, the external permanent magnet 25a would be moved from the magnet position B141 to a magnet position B143. In this case, however, due to the influence of the ferromagnetic material 25f, the posture of the actual capsule endoscope 10 deviates in the elevation angle to be located at a capsule position A143. The correction elevation angle (direction C142) of the external permanent magnet 25a for correcting the deviation amount in the elevation angle is recorded in advance in the database of the storage unit 27. Accordingly, the controller 26 reads the correction elevation angle from the storage unit 27, controls the planar position changing unit 25b and the elevation angle changing unit 25d, and moves the external permanent magnet 25a from the magnet position B141 to the magnet position B142. As a result, the capsule endoscope 10 moves from the capsule position A141 to the capsule position A142.

As illustrated in Example 4, the influence of the ferromagnetic material 25f is changed with the movement of the capsule endoscope 10 in the horizontal direction. Accordingly, the elevation angle of the capsule endoscope 10 might deviate in some cases. In this case, by correcting the elevation angle of the external permanent magnet 25a, it is possible to guide the capsule endoscope 10 to the target posture.

Example 5

Figure 13:
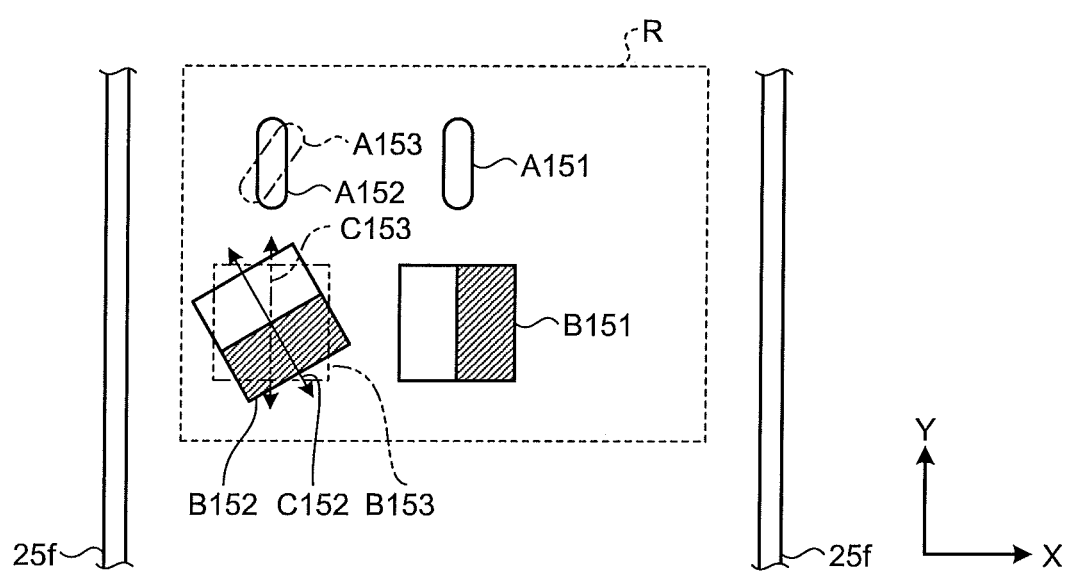
FIG. 13 is a diagram for explaining a method for controlling an external permanent magnet of a guidance apparatus according to Example 5.

A method for controlling the external permanent magnet 25a by the controller 26 of the guidance apparatus 20 according to Example 5 will be described. FIG. 13 is a diagram for explaining a method for controlling the external permanent magnet of the guidance apparatus according to Example 5. FIG. 13 is a top view of the capsule endoscope 10 and the external permanent magnet 25a. As illustrated in FIG. 13, the guidance apparatus 20 according to Example 5 corrects the pivot angle of the external permanent magnet 25a so as to offset or reduce the influence of the ferromagnetic material 25f on the pivot angle of the capsule endoscope 10. Specifically, in a case of moving the capsule endoscope 10 from a capsule position A151 to a capsule position A152 as a target position and target posture (moving in the horizontal direction), the external permanent magnet 25a is moved from a magnet position B151 to a magnet position B152 that has been corrected to offset or reduce the influence of the ferromagnetic material 25f (deviation in pivot angle).

That is, in the guidance apparatus 20, in a case where the external permanent magnet 25a and the ferromagnetic material 25f are brought closer to each other and the influence of the ferromagnetic material 25f is increased when the capsule endoscope 10 is guided to the target position and the target posture, the magnetic pole direction of the external permanent magnet 25a is directed to the ferromagnetic material 25f (toward the left direction on the page in FIG. 13). Specifically, the magnetic pole direction of the external permanent magnet 25a is rotated from a direction C153 to a direction C152.

Next, operation of the guidance apparatus 20 according to Example 5 will be described. First, it is assumed that the capsule endoscope 10 is moved from the capsule position A151 to the capsule position A152, that is, the target position and the target posture. At this time, unless the influence of the ferromagnetic material 25f is taken into consideration, the external permanent magnet 25a would be moved from the magnet position B151 to the magnet position B153. In this case, however, due to the influence of the ferromagnetic material 25f, the posture of the actual capsule endoscope 10 deviates in the pivot angle to be located at a capsule position A153. The correction pivot angle (direction C152) of the external permanent magnet 25a for correcting the deviation amount in the pivot angle is recorded in advance in the database of the storage unit 27. Accordingly, the controller 26 reads the correction pivot angle from the storage unit 27, controls the planar position changing unit 25b and the pivot angle changing unit 25e, and moves the external permanent magnet 25a from the magnet position B151 to the magnet position B152. As a result, the capsule endoscope 10 moves from the capsule position A151 to the capsule position A152.

As illustrated in Example 5, the influence of the ferromagnetic material 25f is changed with the movement of the capsule endoscope 10 in the horizontal direction. Accordingly, the pivot angle of the capsule endoscope 10 might deviate in some cases. In this case, by correcting the pivot angle of the external permanent magnet 25a, it is possible to guide the capsule endoscope 10 to the target posture.

Example 6

A method for controlling the external permanent magnet 25a by the controller 26 of the guidance apparatus 20 according to Example 6 will be described. FIG. 14 is a diagram for explaining a method for controlling the external permanent magnet of the guidance apparatus according to Example 6. As illustrated in FIG. 14, in the guidance apparatus 20 according to Example 6 corrects the position of the external permanent magnet 25a in the horizontal direction so as to offset or reduce the influence of the ferromagnetic material 25f on the horizontal position of the capsule endoscope 10. Specifically, in a case of moving the capsule endoscope 10 from a capsule position A161 to a capsule position A162 as a target position (moving in the vertical direction), the external permanent magnet 25a is moved from the magnet position B161 to a magnet position B162 that has been corrected to offset or reduce the influence of the ferromagnetic material 25f (positional deviation in the horizontal direction).

That is, in the guidance apparatus 20, when the influence of the ferromagnetic material 25f increases when the capsule endoscope 10 is moved in the vertical direction, the external permanent magnet 25a is brought closer to the ferromagnetic material 25f.

Next, operation of the guidance apparatus 20 according to Example 6 will be described. First, it is assumed that the capsule endoscope 10 is moved from the capsule position A161 to the capsule position A162, that is, the target position. At this time, unless the influence of the ferromagnetic material 25f is taken into consideration, the external permanent magnet 25a would be moved from the magnet position B161 to a magnet position B163. In this case, however, due to the influence of the ferromagnetic material 25$f$, the position of the actual capsule endoscope 10 deviates in the horizontal direction to be located at a capsule position A163. The correction horizontal position (magnet position B162) of the external permanent magnet 25$a$ for correcting the deviation amount of the position in the horizontal direction is recorded in advance in the database of the storage unit 27. Accordingly, the controller 26 reads the correction horizontal position from the storage unit 27, controls the planar position changing unit 25$b$ and the vertical position changing unit 25$c$, and moves the external permanent magnet 25$a$ from the magnet position B161 to the magnet position B162. As a result, the capsule endoscope 10 moves from the capsule position A161 to the capsule position A162.

As illustrated in Example 6, the influence of the ferromagnetic material 25$f$ is changed with the movement of the capsule endoscope 10 in the vertical direction. Accordingly, the position of the capsule endoscope 10 in the horizontal direction might deviate in some cases. In this case, by bringing the external permanent magnet 25$a$ closer to the ferromagnetic material 25$f$ with the movement of the capsule endoscope 10 in the vertical direction, it is possible to guide the capsule endoscope 10 to the target position.

Example 7

Figure 15:
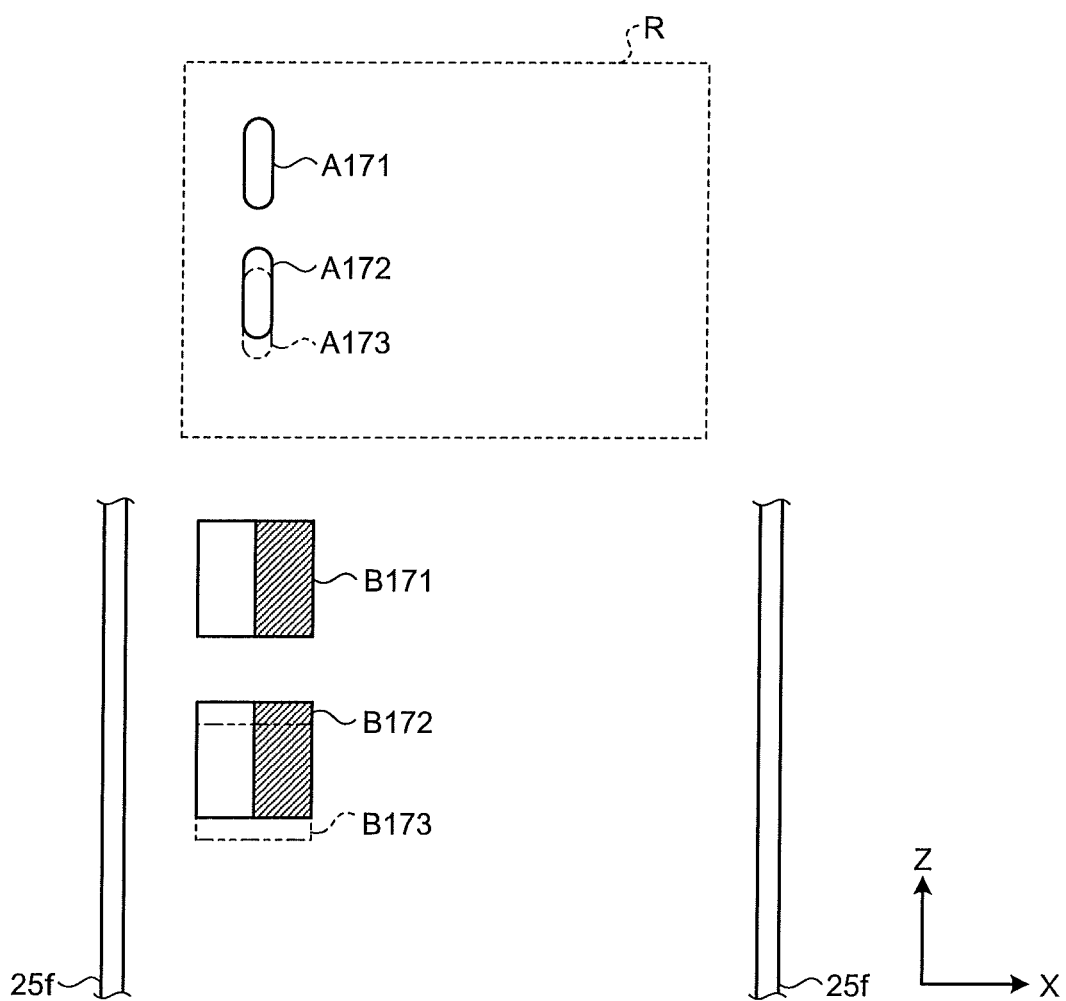
FIG. 15 is a diagram for explaining a method for controlling an external permanent magnet of a guidance apparatus according to Example 7.

A method for controlling the external permanent magnet 25$a$ by the controller 26 of the guidance apparatus 20 according to Example 7 will be described. FIG. 15 is a diagram for explaining a method for controlling the external permanent magnet of the guidance apparatus according to Example 7. As illustrated in FIG. 15, the guidance apparatus 20 according to Example 7 corrects the position of the external permanent magnet 25$a$ in the vertical direction so as to offset or reduce the change in the magnetic force acting on the capsule endoscope 10 due to the ferromagnetic material 25$f$. Specifically, in a case of moving the capsule endoscope 10 from a capsule position A171 to a capsule position A172 as a target position (moving in the vertical direction), the external permanent magnet 25$a$ is moved from a magnet position B171 to a magnet position B172 that has been corrected to offset or reduce the change in the magnetic force acting on the capsule endoscope 10 due to the ferromagnetic material 25$f$.

That is, in the guidance apparatus 20, when the influence of the ferromagnetic material 25$f$ increases when the capsule endoscope 10 is moved downward in the vertical direction, the distance between the capsule endoscope 10 and the external permanent magnet 25$a$ is decreased.

Next, operation of the guidance apparatus 20 according to Example 7 will be described. First, it is assumed that the capsule endoscope 10 is moved from the capsule position A171 to the capsule position A172, that is, the target position. At this time, unless the change in the magnetic force of the ferromagnetic material 25$f$ is taken into consideration, the external permanent magnet 25$a$ would be moved from the magnet position B171 to a magnet position B173. In this case, however, due to the change in the magnetic force of the ferromagnetic material 25$f$, the actual capsule endoscope 10 sinks in the vertical direction to be located at a capsule position A173. The correction vertical position (magnet position B172) amount of the external permanent magnet 25$a$ for correcting the change in the magnetic force in the vertical direction is recorded in advance in the database of the storage unit 27. Accordingly, the controller 26 reads the correction vertical position from the storage unit 27 and controls the vertical position changing unit 25$c$ and moves the external permanent magnet 25$a$ from the magnet position B171 to the magnet position B172. As a result, the capsule endoscope 10 moves from the capsule position A171 to the capsule position A172.

As illustrated in Example 7, the influence of the ferromagnetic material 25$f$ is changed with the movement of the capsule endoscope 10 in the vertical direction. Accordingly, the position of the capsule endoscope 10 in the vertical direction might deviate in some cases. In this case, by decreasing the distance between the capsule endoscope 10 and the external permanent magnet 25$a$ with the movement of the capsule endoscope 10 downward in the vertical direction, it is possible to guide the capsule endoscope 10 to the target position.

Example 8

A method for controlling the external permanent magnet 25$a$ by the controller 26 of the guidance apparatus 20 according to Example 8 will be described. FIG. 16 is a diagram for explaining a method for controlling the external permanent magnet of the guidance apparatus according to Example 8. As illustrated in FIG. 16, the guidance apparatus 20 according to Example 8 corrects the elevation angle of the external permanent magnet 25$a$ so as to offset or reduce the influence of the ferromagnetic material 25$f$ on the elevation angle of the capsule endoscope 10. Specifically, in a case of moving the capsule endoscope 10 from a capsule position A181 to a capsule position A182 as a target position and target posture (moving in the vertical direction), the external permanent magnet 25$a$ is moved from a magnet position B181 to a magnet position B182 that has been corrected to offset or reduce the influence of the ferromagnetic material 25$f$ (deviation in elevation angle).

That is, in the guidance apparatus 20, in a case where the external permanent magnet 25$a$ and the ferromagnetic material 25$f$ are brought closer to each other and the influence of the ferromagnetic material 25$f$ is increased by the movement of the external permanent magnet 25$a$ downward in the vertical direction when the capsule endoscope 10 is guided to the target position and the target posture, the inclination of the magnetic pole direction of the external permanent magnet 25$a$ with respect to the horizontal plane is increased. Specifically, the magnetic pole direction of the external permanent magnet 25$a$ is rotated from a direction C183 to a direction C182.

Next, operation of the guidance apparatus 20 according to Example 8 will be described. First, it is assumed that the capsule endoscope 10 is moved from the capsule position A181 to the capsule position A182, that is, the target position and the target posture. At this time, unless the influence of the ferromagnetic material 25$f$ is taken into consideration, the external permanent magnet 25$a$ would be moved from the magnet position B181 to a magnet position B183. In this case, however, due to the influence of the ferromagnetic material 25$f$, the posture of the actual capsule endoscope 10 deviates in the elevation angle to be located at a capsule position A183. The correction elevation angle (direction C182) of the external permanent magnet 25$a$ that corrects the deviation amount of the elevation angle is recorded in advance in the database of the storage unit 27. Accordingly, the controller 26 reads the correction elevation angle from the storage unit 27, controls the vertical position changing unit 25$c$ and the elevation angle changing unit 25$d$, and moves the external permanent magnet 25$a$ from the magnet position B181 to the magnet position B182. As a result, the capsule endoscope 10 moves from the capsule position A181 to the capsule position A182.

As illustrated in Example 8, the influence of the ferromagnetic material 25f is changed with the movement of the capsule endoscope 10 in the vertical direction. Accordingly, the elevation angle of the capsule endoscope 10 might deviate in some cases. In this case, by correcting the elevation angle of the external permanent magnet 25a, it is possible to guide the capsule endoscope 10 to the target posture.

Similarly to Example 8, the influence of the ferromagnetic material 25f is changed with the movement of the capsule endoscope 10 in the vertical direction. Accordingly, the pivot angle of the capsule endoscope 10 might deviate in some cases. In this case, by correcting the pivot angle of the external permanent magnet 25a, it is possible to guide the capsule endoscope 10 to the target posture.

Example 9

Figure 17:
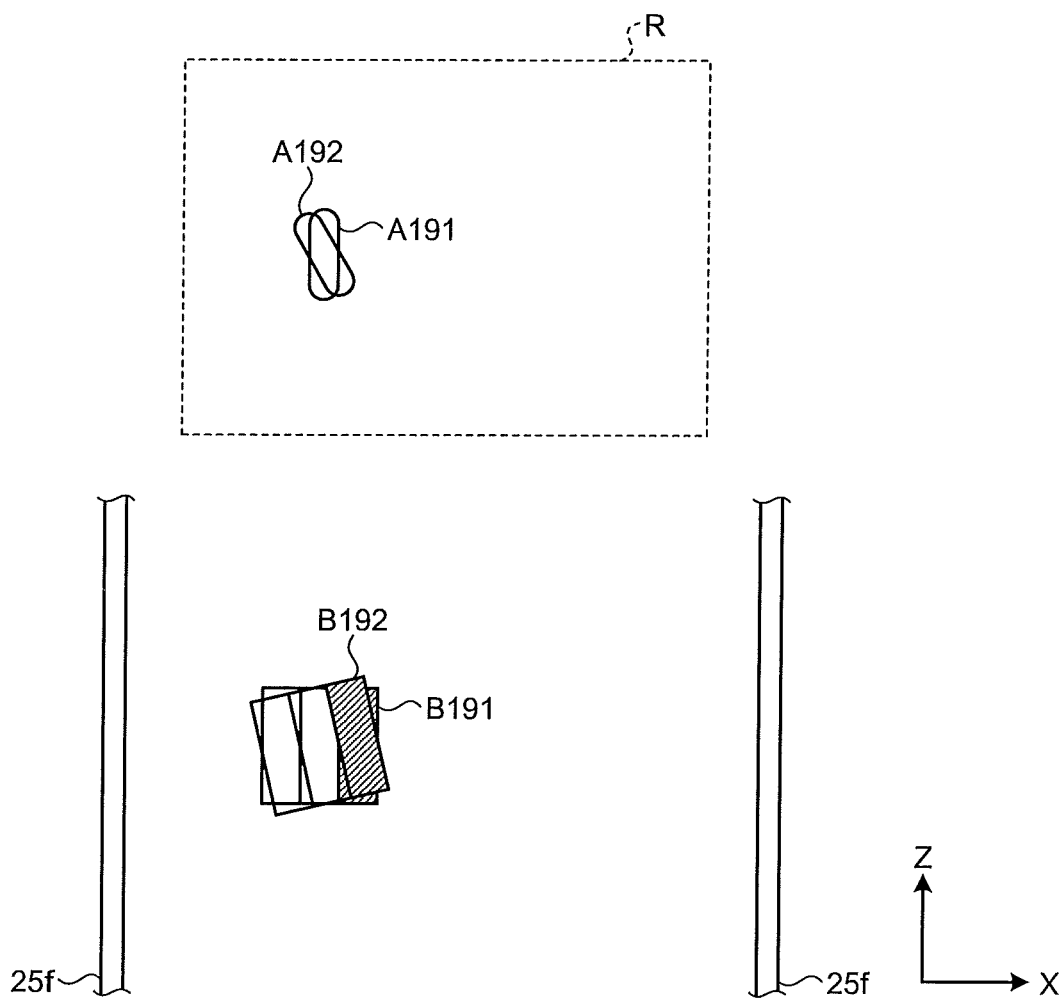
FIG. 17 is a diagram for explaining a method for controlling an external permanent magnet of a guidance apparatus according to Example 9.
Figure 18:
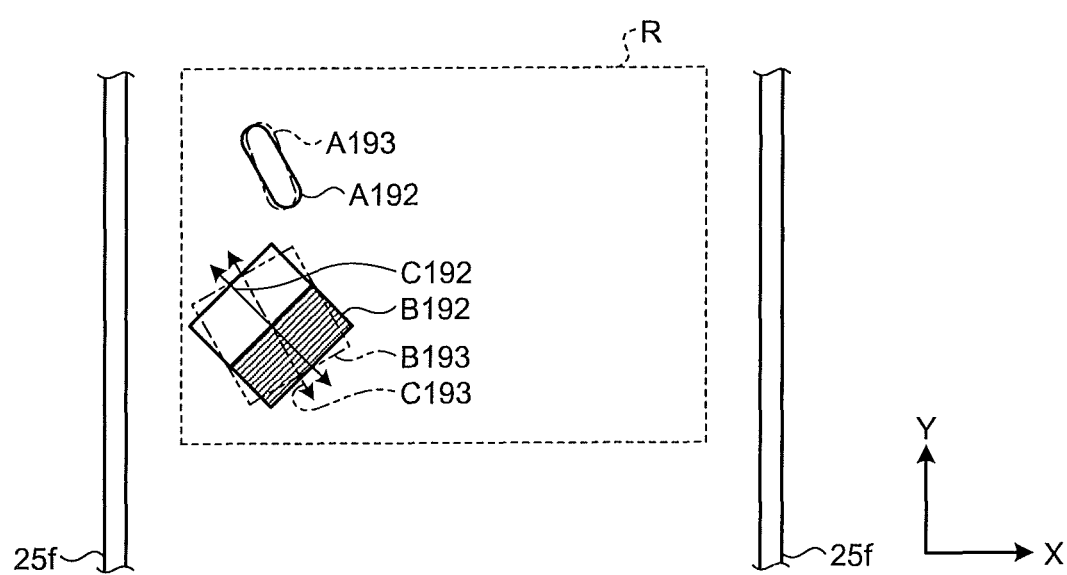
FIG. 18 is a diagram for explaining a method for controlling an external permanent magnet of a guidance apparatus according to Example 9.

A method for controlling the external permanent magnet 25a by the controller 26 of the guidance apparatus 20 according to Example 9 will be described. FIGS. 17 and 18 are diagrams for explaining a method for controlling the external permanent magnet of the guidance apparatus according to Example 9. FIG. 17 is a side view of the capsule endoscope 10 and the external permanent magnet 25a, and FIG. 18 is a top view thereof. As illustrated in FIGS. 17 and 18, the guidance apparatus 20 according to Example 9 corrects the pivot angle of the external permanent magnet 25a so as to offset or reduce the influence of the ferromagnetic material 25f on the pivot angle of the capsule endoscope 10. Specifically, in a case of moving the capsule endoscope 10 from a capsule position A191 to a capsule position A192 as a target posture (changing elevation angle), the external permanent magnet 25a is moved from a magnet position B191 to a magnet position B192 that has been corrected to offset or reduce the influence of the ferromagnetic material 25f (deviation in pivot angle).

That is, in the guidance apparatus 20, in a case where the inclination of the magnetic pole direction of the external permanent magnet 25a with respect to the horizontal plane increases and the influence of the ferromagnetic material 25f is increased when the capsule endoscope 10 is guided to the target posture, the magnetic pole direction of the external permanent magnet 25a is directed to the ferromagnetic material 25f (toward the left direction on the page in FIG. 18). Specifically, the magnetic pole direction of the external permanent magnet 25a is rotated from a direction C193 to a direction C192.

Next, operation of the guidance apparatus 20 according to Example 9 will be described. First, it is assumed that the capsule endoscope 10 is moved from the capsule position A191 to the capsule position A192, that is, the target posture. At this time, unless the influence of the ferromagnetic material 25f is taken into consideration, the external permanent magnet 25a would be moved from the magnet position B191 to a magnet position B193. In this case, however, due to the influence of the ferromagnetic material 25f, the posture of the actual capsule endoscope 10 deviates in the pivot angle to be located at a capsule position A193. The correction pivot angle (direction C192) of the external permanent magnet 25a for correcting the deviation amount of the pivot angle is recorded in advance in the database of the storage unit 27. Accordingly, the controller 26 reads the correction pivot angle from the storage unit 27, controls the elevation angle changing unit 25d and the pivot angle changing unit 25e, and moves the external permanent magnet 25a from the magnet position B191 to the magnet position B192. As a result, the capsule endoscope 10 moves from the capsule position A191 to the capsule position A192.

As illustrated in Example 9, the influence of the ferromagnetic material 25f is changed with the change in the elevation angle of the capsule endoscope 10. Accordingly, the pivot angle of the capsule endoscope 10 might deviate in some cases. In this case, by correcting the pivot angle of the external permanent magnet 25a, it is possible to guide the capsule endoscope 10 to the target posture.

Moreover, similarly to Example 9, the influence of the ferromagnetic material 25f is changed with the change in the elevation angle of the capsule endoscope 10. Accordingly, the elevation angle of the capsule endoscope 10 might deviate in some cases. In this case, by correcting the elevation angle of the external permanent magnet 25a, it is possible to guide the capsule endoscope 10 to the target posture.

Furthermore, similarly to Example 9, the influence of the ferromagnetic material 25f is changed with the change in the elevation angle of the capsule endoscope 10. Accordingly, the position of the capsule endoscope 10 in the horizontal direction and the vertical direction might deviate in some cases. In this case, by correcting the position of the external permanent magnet 25a in the horizontal direction and the vertical direction, it is possible to guide the capsule endoscope 10 to the target position.

Moreover, the influence of the ferromagnetic material 25f is changed with the change in the pivot angle of the capsule endoscope 10. Accordingly, the position in the horizontal direction and the position in the vertical direction, the elevation angle, and the pivot angle of the capsule endoscope 10 might deviate in some cases. In this case, similarly to Example 9, by correcting the position in the horizontal direction and the position in the vertical direction, the elevation angle, and the pivot angle of the external permanent magnet 25a, it is possible to guide the capsule endoscope 10 to the target position and the target posture.

Example 10

Figure 19:
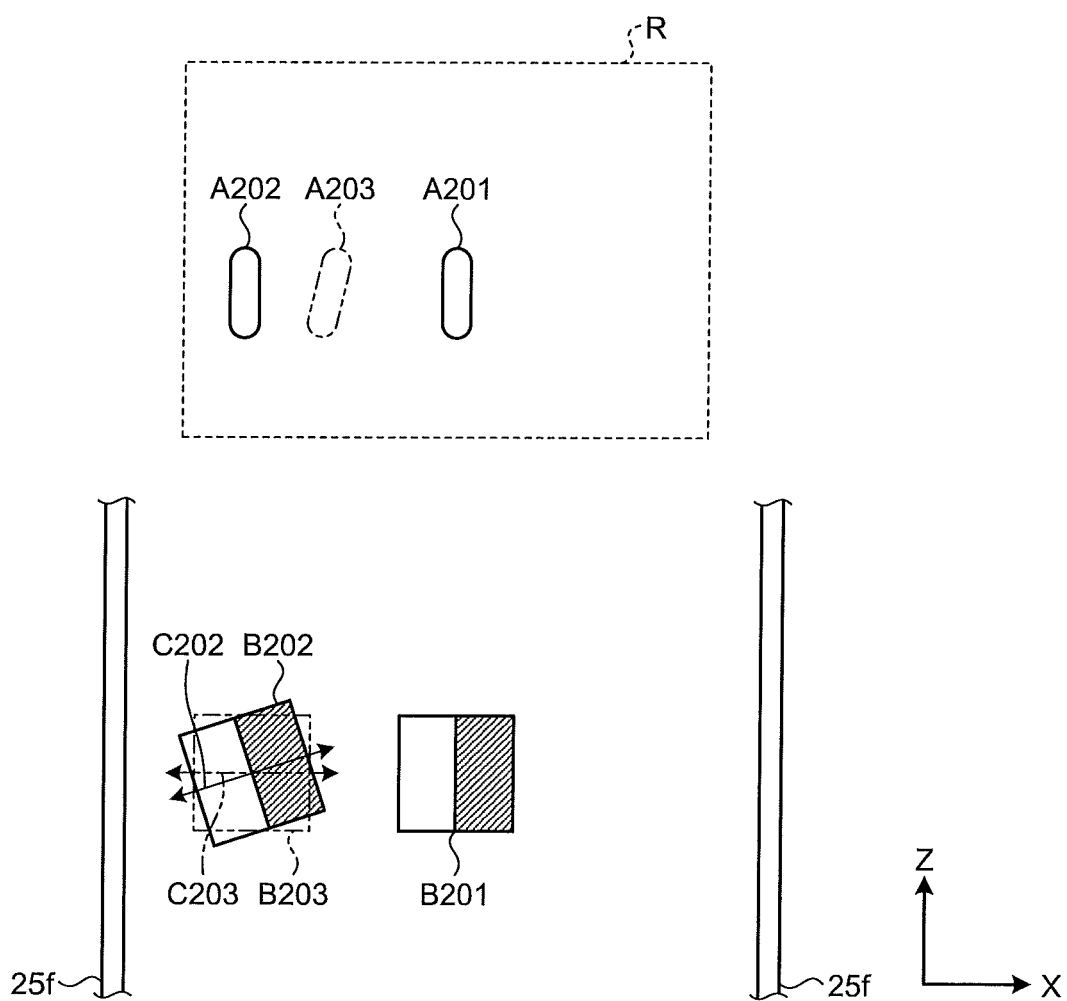
FIG. 19 is a diagram for explaining a method for controlling an external permanent magnet of a guidance apparatus according to Example 10.

A method for controlling the external permanent magnet 25a by the controller 26 of the guidance apparatus 20 according to Example 10 will be described. FIG. 19 is a diagram for explaining a method for controlling the external permanent magnet of the guidance apparatus according to Example 10. As illustrated in FIG. 19, the guidance apparatus 20 according to Example 10 corrects the elevation angle of the external permanent magnet 25a so as to offset or reduce the influence of the ferromagnetic material 25f on the horizontal position and the elevation angle of the capsule endoscope 10. More specifically, in a case of moving the capsule endoscope 10 from the capsule position A201 to a capsule position A202 as a target position (moving in the horizontal direction), the external permanent magnet 25a is moved from a magnet position B201 to a magnet position B202 that has been corrected to offset or reduce the influence of the ferromagnetic material 25f (deviation of the position in the horizontal direction, and deviation of the elevation angle).

That is, in the guidance apparatus 20, in a case where the external permanent magnet 25a and the ferromagnetic material 25f are brought closer to each other and the influence of the ferromagnetic material 25f is increased when the capsule endoscope 10 is guided to the target position and the target posture, the inclination of the magnetic pole direction of the external permanent magnet 25a with respect to the horizontal plane is increased. Specifically, the magnetic pole direction of the external permanent magnet 25a is rotated from a direction C203 to a direction C202.

Next, operation of the guidance apparatus 20 according to Example 10 will be described. First, it is assumed that the capsule endoscope 10 is moved from the capsule position A201 to the capsule position A202, that is, the target position. At this time, unless the influence of the ferromagnetic material 25f is taken into consideration, the external permanent magnet 25a would be moved from the magnet position B201 to a magnet position B203. In this case, however, due to the influence of the ferromagnetic material 25f, the position in the horizontal direction and the elevation angle of the actual capsule endoscope 10 deviates to be located at a capsule position A203. The correction elevation angle (direction C202) of the external permanent magnet 25a for correcting the deviation amount in the position in the horizontal direction and in the elevation angle is recorded in advance in the database of the storage unit 27. Accordingly, the controller 26 reads the correction elevation angle from the storage unit 27, controls the planar position changing unit 25b and the elevation angle changing unit 25d, and moves the external permanent magnet 25a from the magnet position B201 to the magnet position B202. As a result, the capsule endoscope 10 moves from the capsule position A201 to the capsule position A202.

As illustrated in Example 10, the position in the horizontal direction and the elevation angle might deviate due to the influence of the ferromagnetic material 25f, in some cases. In this case, by correcting solely the elevation angle of the external permanent magnet 25a, it is possible to guide the capsule endoscope 10 to the target position and the target posture. Similarly, it is allowable to configure such that, by correcting any one of the position in the horizontal direction, the position in the vertical direction, the elevation angle, and the pivot angle of the external permanent magnet 25a, two or more positions or postures are corrected.

Example 11

Figure 20:
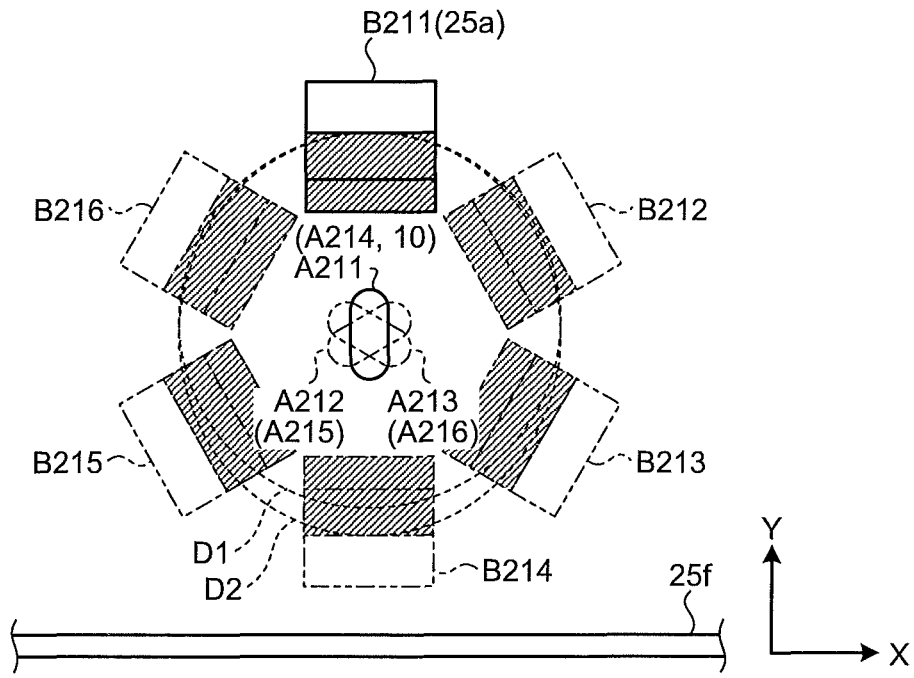
FIG. 20 is a diagram for explaining a method for controlling an external permanent magnet of a guidance apparatus according to Example 11.

A method for controlling the external permanent magnet 25a by the controller 26 of the guidance apparatus 20 according to Example 11 will be described. FIG. 20 is a diagram for explaining a method for controlling the external permanent magnet of the guidance apparatus according to Example 11. FIG. 20 is a top view of the capsule endoscope 10 and the external permanent magnet 25a. As illustrated in FIG. 20, the guidance apparatus 20 according to Example 11 fully rotates the pivot angle of the capsule endoscope 10. Specifically, the capsule endoscope 10 is fully rotated in order of the capsule positions A211, A212, A213, A214, A215, A216, and A211. At this time, in a case where the influence of the ferromagnetic material 25f on the horizontal position of the capsule endoscope 10 is not taken into consideration, the external permanent magnet 25a would be moved in a circle along a locus D1. However, due to the influence of the ferromagnetic material 25f on the horizontal position of the capsule endoscope 10, positional deviation in the horizontal direction of the capsule endoscope 10 occurs. Accordingly, the guidance apparatus 20 corrects the position of the external permanent magnet 25a in the horizontal direction and moves the external permanent magnet 25a along a locus D2 so as to offset or reduce the influence of the ferromagnetic material 25f. Specifically, the external permanent magnet 25a is moved in order of the magnet positions B211, B212, B213, B214, B215, B216, and B211. As a result, the pivot angle of the capsule endoscope 10 is rotated 360 degrees.

Example 12

Figure 21:
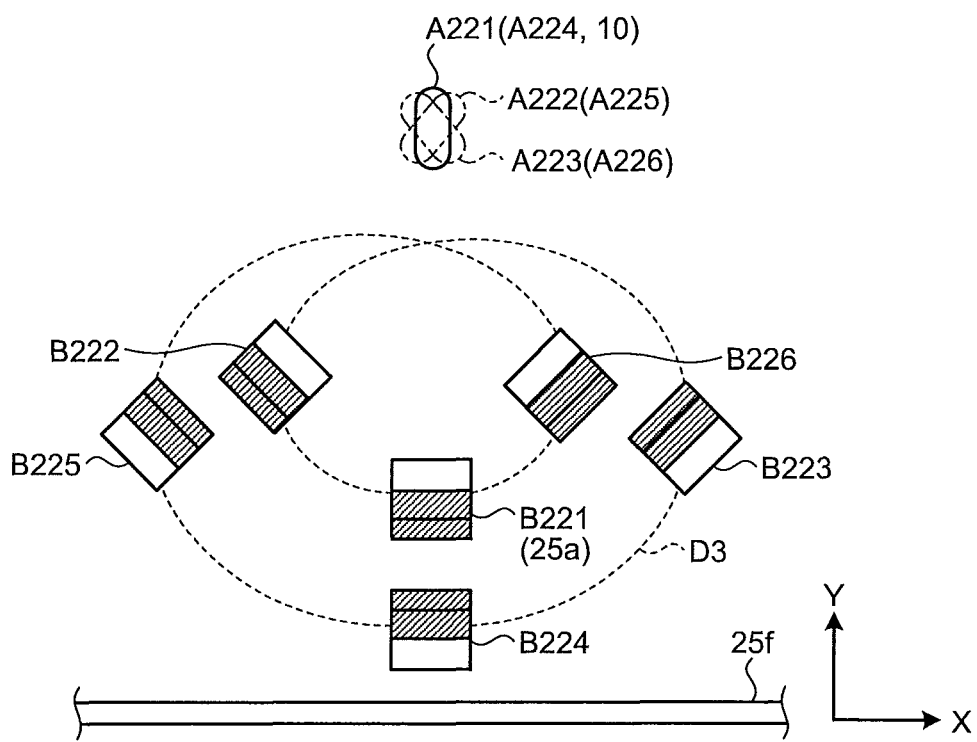
FIG. 21 is a diagram for explaining a method for controlling an external permanent magnet of a guidance apparatus according to Example 12.

A method for controlling the external permanent magnet 25a by the controller 26 of the guidance apparatus 20 according to Example 12 will be described. FIG. 21 is a diagram for explaining a method for controlling the external permanent magnet of the guidance apparatus according to Example 12. FIG. 21 is a top view of the capsule endoscope 10 and the external permanent magnet 25a. As illustrated in FIG. 21, the guidance apparatus 20 according to Example 12 fully rotates the pivot angle of the capsule endoscope 10, similarly to Example 11. In a case, however, where the capsule endoscope 10 and the external permanent magnet 25a are close to the ferromagnetic material 25f, and the influence of the ferromagnetic material 25f on the horizontal position of the capsule endoscope 10 is great, there is a need to move the external permanent magnet 25a two rounds in a predetermined curved line such as a locus D3 as illustrated in FIG. 21. Specifically, the external permanent magnet 25a is moved in the order of the magnet positions B221, B222, B223, B224, B225, B226, and B221. As a result, the capsule endoscope 10 rotates in the order of the capsule positions A221, A222, A223, A224, A225, A226, and A211, and the pivot angle is rotated 360 degrees.

Note that instead of the external permanent magnet 25a, the magnetic field generator 25 may include a plurality of electromagnets, a power supply unit for supplying electric power to the individual electromagnets, a current controller for controlling a current flowing through individual electromagnets under the control of the controller 26. In this case, the magnetic field generator 25 may correct the position of the electromagnet or correct the current flowing through individual electromagnets so as to offset or reduce the influence of the magnetic field shielding material.

According to some embodiments, it is possible to realize a guidance apparatus and a capsule medical apparatus guidance system capable of guiding a capsule medical apparatus to a target position and posture in the guidance apparatus of a capsule medical apparatus including a magnetic field shielding material.

Further effects and variations can be easily derived by those skilled in the art. Thus, the broader aspects of the disclosure are not limited to the specific details and representative embodiments illustrated and described as such. Accordingly, various modifications are possible without departing from the spirit or scope of the general inventive concept as defined by the appended claims and their equivalents.

What is claimed is:

1. A guidance apparatus configured to guide a capsule medical apparatus by a magnetic field, the capsule medical apparatus being configured to be introduced into a subject and includes an internal magnet, the guidance apparatus comprising:
   a magnetic field generator configured to generate a magnetic field that acts on the magnet for guiding the capsule medical apparatus to at least one of a target position and a target posture;
   a magnetic field shielding material configured to shield the magnetic field generated by the magnetic field generator;
   a storage in which first information relating to a deviation amount of at least one of a position and a posture of the capsule medical apparatus with respect to at least one of the target position and the target posture is stored, the deviation amount being caused by distortion of the magnetic field due to the magnetic field shielding material; and a controller configured to:
- receive second information of at least one of the target position and the target posture for guiding the capsule medical apparatus to at least one of the target position and the target posture;
- read the first information from the storage in accordance with the received at least one of the target position and the target posture;
- control the magnetic field generator to generate a magnetic field that has been corrected to offset or reduce the deviation amount by using the read first information; and
- change a position of the magnetic field generator with respect to the target position so as to generate the magnetic field that has been corrected to offset or reduce the deviation amount.

2. The guidance apparatus according to claim 1, wherein, when the capsule medical apparatus is guided to the target position, the controller is configured to increase a moving amount of the magnetic field generator toward the magnetic field shielding material in accordance with movement of bringing the target position closer to the magnetic field shielding material.

3. The guidance apparatus according to claim 1, wherein, when the capsule medical apparatus is guided to the target position, the controller is configured to increase a moving amount of the magnetic field generator toward a direction opposite to a gravity direction in accordance with movement of bringing the target position closer to the magnetic field shielding material.

4. The guidance apparatus according to claim 2, wherein, when the capsule medical apparatus is guided to the target position, the controller is configured to:
- move the magnetic field generator so as to increase a speed of the magnetic field generator in a case of bringing the magnetic field generator closer to the magnetic field shielding material; and
- move the magnetic field generator so as to decrease the speed of the magnetic field generator in a case of bringing the magnetic field generator away from the magnetic field shielding material.

5. The guidance apparatus according to claim 1, wherein, when the capsule medical apparatus is guided to the target position, the controller is configured to increase a moving amount of the magnetic field generator toward the magnetic field shielding material in accordance with movement of the target position in a gravity direction.

6. The guidance apparatus according to claim 1, wherein, when the capsule medical apparatus is guided to the target position, the controller is configured to decrease a moving amount of the magnetic field generator in a gravity direction in accordance with movement of the target position in the gravity direction.

7. A guidance apparatus configured to guide a capsule medical apparatus by a magnetic field, the capsule medical apparatus being configured to be introduced into a subject and includes an internal magnet, the guidance apparatus comprising:
- a magnetic field generator configured to generate a magnetic field that acts on the magnet for guiding the capsule medical apparatus to at least one of a target position and a target posture;
- a magnetic field shielding material configured to shield the magnetic field generated by the magnetic field generator;
- a storage in which first information relating to a deviation amount of at least one of a position and a posture of the capsule medical apparatus with respect to at least one of the target position and the target posture is stored, the deviation amount being caused by distortion of the magnetic field due to the magnetic field shielding material; and a controller configured to:
- receive second information of at least one of the target position and the target posture for guiding the capsule medical apparatus to at least one of the target position and the target posture;
- read the first information from the storage in accordance with the received at least one of the target position and the target posture;
- control the magnetic field generator to generate a magnetic field that has been corrected to offset or reduce the deviation amount by using the read first information; and
- change an angle of the magnetic field generator with respect to the capsule medical apparatus so as to generate a magnetic field that has been corrected to offset or reduce the deviation amount.

8. The guidance apparatus according to claim 7, wherein, when the capsule medical apparatus is guided to the target position, the controller is configured to increase an inclination of a magnetic pole direction of the magnetic field generator with respect to a plane orthogonal to a gravity direction in accordance with movement of bringing the target position closer to the magnetic field shielding material.

9. The guidance apparatus according to claim 7, wherein, when the capsule medical apparatus is guided to the target position, the controller is configured to increase an inclination of a magnetic pole direction of the magnetic field generator with respect to a plane orthogonal to a gravity direction in accordance with movement of the target position in the gravity direction.

10. The guidance apparatus according to claim 7, wherein, when the capsule medical apparatus is guided to the target position, the controller is configured to direct a magnetic pole direction of the magnetic field generator toward the magnetic field shielding material that is in closest proximity with the magnetic field generator within a plane orthogonal to a gravity direction in accordance with movement of bringing the target position closer to the magnetic field shielding material.

11. The guidance apparatus according to claim 7, wherein, when the capsule medical apparatus is guided to the target posture, the controller is configured to direct a magnetic pole direction of the magnetic field generator toward the magnetic field shielding material in closest proximity with the magnetic field generator within a plane orthogonal to a gravity direction in accordance with an increase of the inclination of the magnetic pole direction of the magnetic field generator with respect to the plane orthogonal to the gravity direction.

12. The guidance apparatus according to claim 7, wherein, when the magnetic field generator is controlled to rotate a longitudinal direction of the capsule medical apparatus within a plane orthogonal to a gravity direction by 360 degrees, the controller is configured to move the magnetic field generator two rounds in a predetermined curved line within the plane orthogonal to the gravity direction.

13. A guidance apparatus configured to guide a capsule medical apparatus by a magnetic field, the capsule medical apparatus being configured to be introduced into a subject and includes an internal magnet, the guidance apparatus comprising:
  a magnetic field generator configured to generate a magnetic field that acts on the magnet for guiding the capsule medical apparatus to at least one of a target position and a target posture;
  a magnetic field shielding material configured to shield the magnetic field generated by the magnetic field generator;
  a storage in which first information relating to a deviation amount of at least one of a position and a posture of the capsule medical apparatus with respect to at least one of the target position and the target posture is stored, the deviation amount being caused by distortion of the magnetic field due to the magnetic field shielding material; and
  a controller configured to:
    receive second information of at least one of the target position and the target posture for guiding the capsule medical apparatus to at least one of the target position and the target posture;
    read the first information from the storage in accordance with the received at least one of the target position and the target posture;
    control the magnetic field generator to generate a magnetic field that has been corrected to offset or reduce the deviation amount by using the read first information;
    calculate an angle of a magnetic pole direction of the magnetic field generator with respect to a direction toward the magnetic field shielding material in closest proximity with the magnetic field generator within a plane orthogonal to a gravity direction so as to generate a magnetic field that has been corrected to offset or reduce the deviation amount to achieve the target posture of the capsule medical apparatus;
    calculate a position of the magnetic field generator so as to generate the magnetic field that has been corrected to offset or reduce the deviation amount to cause the capsule medical apparatus to move to the target position in a case where the magnetic pole direction of the magnetic field generator matches the calculated angle; and
    move the magnetic field generator to the calculated angle and the calculated position.

14. A guidance apparatus configured to guide a capsule medical apparatus by a magnetic field, the capsule medical apparatus being configured to be introduced into a subject and includes an internal magnet, the guidance apparatus comprising:
  a magnetic field generator configured to generate a magnetic field that acts on the magnet for guiding the capsule medical apparatus to at least one of a target position and a target posture;
  a magnetic field shielding material configured to shield the magnetic field generated by the magnetic field generator;
  a storage in which first information relating to a deviation amount of at least one of a position and a posture of the capsule medical apparatus with respect to at least one of the target position and the target posture is stored, the deviation amount being caused by distortion of the magnetic field due to the magnetic field shielding material; and
  a controller configured to:
    receive second information of at least one of the target position and the target posture for guiding the capsule medical apparatus to at least one of the target position and the target posture;
    read the first information from the storage in accordance with the received at least one of the target position and the target posture;
    control the magnetic field generator to generate a magnetic field that has been corrected to offset or reduce the deviation amount by using the read first information;
    calculate an angle of a magnetic pole direction of the magnetic field generator with respect to a plane orthogonal to a gravity direction so as to generate a magnetic field that has been corrected to offset or reduce the deviation amount to achieve the target posture of the capsule medical apparatus;
    calculate a position of the magnetic field generator so as to generate the magnetic field that has been corrected to offset or reduce the deviation amount to cause the capsule medical apparatus to move to the target position in a case where the magnetic pole direction of the magnetic field generator matches the calculated angle; and
    move the magnetic field generator to the calculated angle and the calculated position.

15. The guidance apparatus according to claim 1, wherein the controller is further configured to receive a position and a posture of the capsule medical apparatus in the subject.

16. A capsule medical apparatus guidance system comprising:
  the guidance apparatus according to claim 1; and
  a capsule medical apparatus including a magnet being internally arranged.

17. The capsule medical apparatus guidance system according to claim 16, wherein the capsule medical apparatus includes:
  a capsule-shaped casing configured to be introduced inside a subject; and
  a permanent magnet encapsulated in the capsule-shaped casing, and
  wherein the permanent magnet is arranged such that a center of gravity of the capsule medical apparatus and a geometrical center of the capsule-shaped casing are different from each other, and
  a magnet pole direction of the permanent magnet is different from a direction of a line connecting the center of gravity of the capsule medical apparatus with the geometrical center of the capsule-shaped casing.

* * * * *